(12) United States Patent
Gordon et al.

(10) Patent No.: US 9,242,109 B2
(45) Date of Patent: Jan. 26, 2016

(54) APPARATUS AND METHODS FACILITATING POWER REGULATION FOR AN IMPLANTABLE DEVICE

(71) Applicant: Medtronic, Inc., Minneapolis, MN (US)

(72) Inventors: Charles Gordon, Phoenix, AZ (US); Shohan Hossain, Maple Grove, MN (US); Weizheng Liang, Chandler, AZ (US); James D. Reinke, Maple Grove, MN (US); William D Wildes, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 246 days.

(21) Appl. No.: 13/837,188

(22) Filed: Mar. 15, 2013

(65) Prior Publication Data
US 2014/0277277 A1    Sep. 18, 2014

(51) Int. Cl.
*A61N 1/378* (2006.01)
*A61N 1/372* (2006.01)
*A61N 1/39* (2006.01)

(52) U.S. Cl.
CPC .............. *A61N 1/378* (2013.01); *A61N 1/37276* (2013.01); *A61N 1/3975* (2013.01)

(58) Field of Classification Search
USPC .......................................................... 607/61
See application file for complete search history.

(56) References Cited

U.S. PATENT DOCUMENTS

| 6,023,641 | A | 2/2000 | Thompson |
| 6,091,987 | A | 7/2000 | Thompson |
| 6,154,675 | A | 11/2000 | Juran et al. |
| 6,415,181 | B1 | 7/2002 | Schu et al. |
| 6,434,425 | B1 | 8/2002 | Thompson |
| 6,453,198 | B1 | 9/2002 | Torgerson et al. |
| 6,745,077 | B1 * | 6/2004 | Griffith et al. .................. 607/61 |
| 8,165,692 | B2 | 4/2012 | Strother et al. |
| 8,330,532 | B2 | 12/2012 | Nikolov et al. |
| 2002/0087146 | A1 | 7/2002 | Schu et al. |
| 2014/0077871 | A1 * | 3/2014 | Bernstein ...................... 327/543 |

* cited by examiner

*Primary Examiner* — Carl H Layno
*Assistant Examiner* — Jon Eric C Morales
(74) *Attorney, Agent, or Firm* — Evans M. Mburu

(57) ABSTRACT

Apparatus and methods configured to perform power regulation for an implantable device are presented. In an aspect, an implantable device can include a substrate that forms at least part of a body of the implantable device and a circuit disposed on or within the substrate. The circuit can include a high load power regulator configured to provide a first current level to components of the implantable device and a low load power regulator configured to provide a second current level to components of the implantable device, wherein the second current level is lower that the first current level. The circuit can also include a regulator switch configured to enable or disable current draw from the high load power regulator and the low load power regulator as a function of power state and associated power requirement of the components of the implantable device.

28 Claims, 16 Drawing Sheets

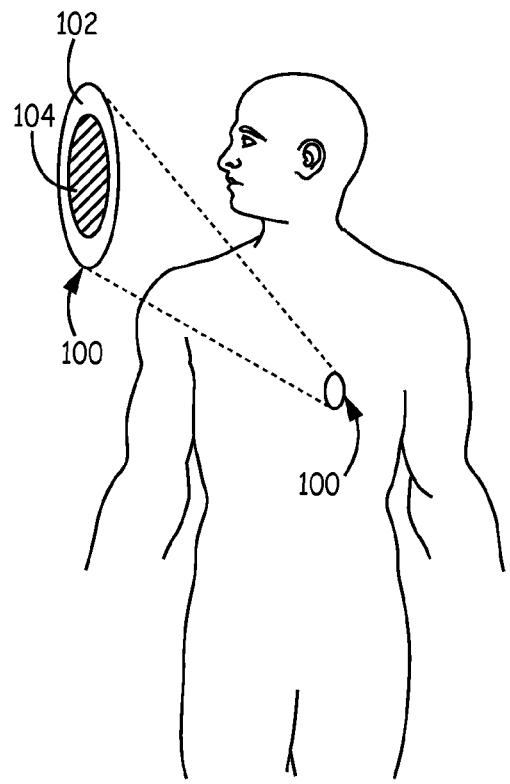
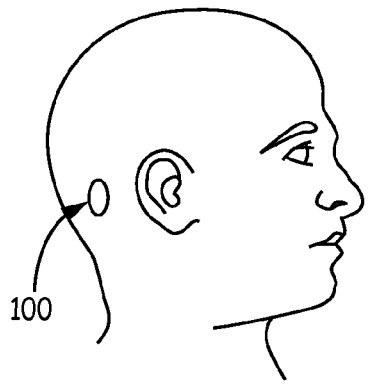
FIG. 1A
FIG. 1B
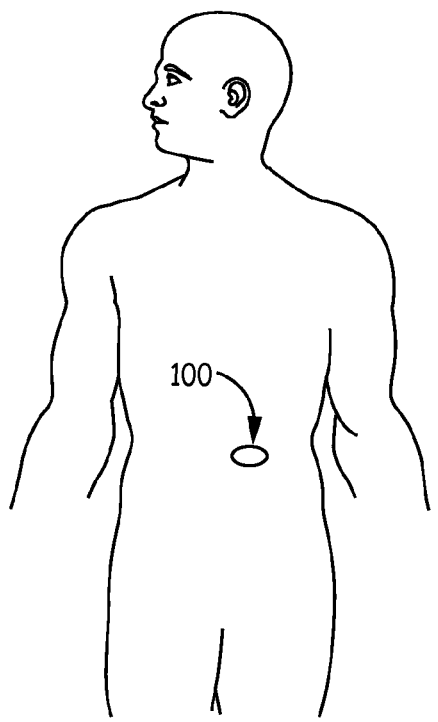
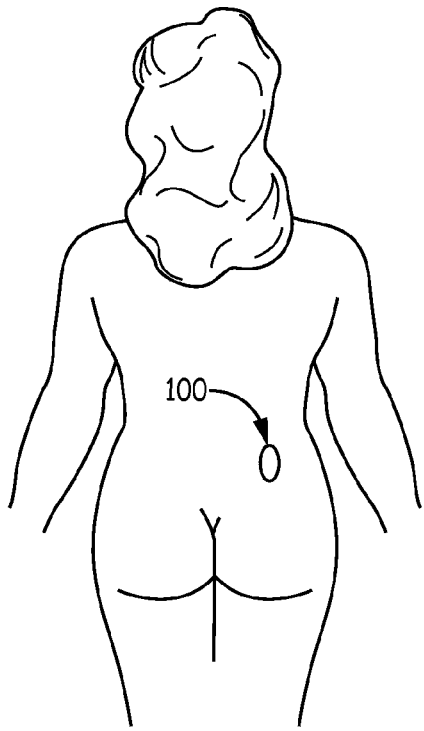
FIG. 1C
FIG. 1D

APPARATUS AND METHODS FACILITATING POWER REGULATION FOR AN IMPLANTABLE DEVICE

TECHNICAL FIELD

This disclosure generally relates to regulating power supplied to components of an implantable device in order to conserve available power.

BACKGROUND

Implantable devices, such as implantable medical devices, are increasing in complexity while shrinking in size. One hurdle to achieving such small and highly functional devices is the challenging ability to efficiently power these devices for a significant period of time. In particular, many implantable devices operate from power sources that have a limited lifetime and cannot be recharged, such as a non-rechargeable battery. After the device is implanted within the human body and the battery dies, the implant often must be removed. Thus, extending life of a battery of an implantable device is highly desirable.

BRIEF DESCRIPTION OF THE DRAWINGS

FIGS. 1A, 1B, 1C and 1D are illustrations of example embodiments of implantable devices implanted on or within a human body in accordance with aspects described herein.

DETAILED DESCRIPTION

Figure 2:
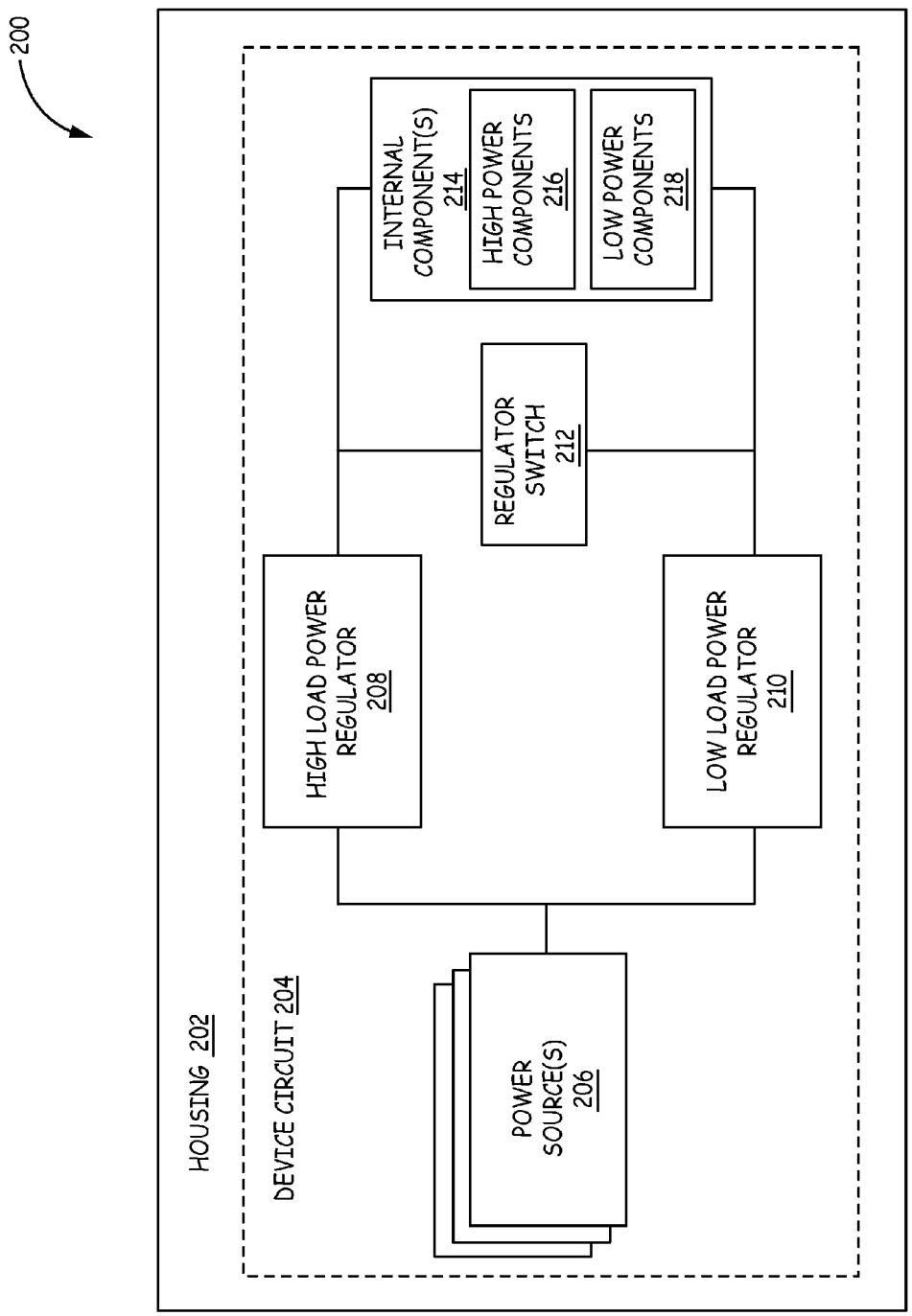
FIG. 2 is an illustration of an example implantable device in accordance with aspects described herein.

Various aspects are now described with reference to the drawings, wherein like reference numerals are used to refer to like elements throughout. In the following description, for purposes of explanation, numerous specific details are set forth in order to provide a more thorough understanding of one or more aspects. However, it should be appreciated that such aspects can be practiced without these specific details. In other instances, structures and devices are shown in block diagram form in order to facilitate describing one or more aspects.

In an embodiment, the disclosed subject matter relates to an implantable device having a regulated power supply. The implantable device can include a substrate that forms at least part of a body of the implantable device and a circuit disposed on or within the substrate. The circuit can include a high load power regulator configured to provide a first current level to one or more components of the implantable device and a low load power regulator configured to provide a second current level to the one or more components of the implantable device, wherein the second current level is lower that the first current level. The circuit further includes a regulator switch configured to enable or disable current draw from the high load power regulator and the low load power regulator as a function of a power state and associated power requirement of the one or more components of the implantable device.

In another embodiment, a power regulation system or circuit for an implantable medical device is disclosed. The power regulation system can include a processor operatively coupled to the implantable medical device, and a non-transitory computer readable medium that stores computer executable components. The system can further include a central processing unit (CPU) power regulator configured to provide a first current level to the processor, an analog power regulator configured to provide a second current level to the processor, wherein the second current level is lower that the first current level, and a regulator switch configured to enable or disable current draw from the CPU power regulator and the analog power regulator as a function of a power state of the processor.

In one or more additional aspects, a method is disclosed that includes providing, via an analog power regulator, a first current level to a processer of an implantable device in response to digital components of the processor being in an off state and receiving a trigger signal indicating a request to turn on digital operation of the digital components. The method further includes the following acts in response to the receiving the trigger signal: turning off operation of the analog power regulator, turning on operation of a central processing unit (CPU) power regulator, turning on the digital operation of the digital components, providing, via the CPU power regulator, a second current level to the processor, wherein the second current level is higher than the first current level, and powering the digital operation of the digital components.

With reference now to the drawings, FIGS. 1A-1D are illustrations of example embodiments of implantable devices 100 implanted on or within a human body in accordance with aspects described herein. The subject disclosure provides power regulation schemes that can be employed in various electronic devices. Implantable devices, such as implantable medical devices, are particularly suited for the subject power regulation schemes because many implantable devices operate off of one or more batteries. After the device is implanted within the human body and the battery dies, the implant often must be removed. Thus, extending life of a battery of an implantable device is highly desirable. The type of implantable devices capable of employing the subject power regulation schemes to extend device longevity can vary in function, size, shape and material. For example, implantable device 100 can include but is not limited to: a leaded implantable pacemaker, a defibrillator, a nerve stimulator, a miniature leadless pacemaker and a diagnostic device.

In an aspect, the implantable devices described herein, such as implantable device 100, include at least a housing 102 and a device circuit 104 located within the housing 102. In an aspect, the device circuit 104 is formed on or within a substrate that is placed inside a biocompatible housing 102. The device circuit 104 includes one or more power sources, such as a battery, one or more device electrical components that are powered via the one or more power sources and power regulation circuitry that facilitates regulating power provided to the one or more device components from the one or more power sources. The device circuit 104 is described in greater detail with respect to FIGS. 2-9.

In an aspect, implantable device 100 (and those additionally described herein), strive to achieve significantly small size while maintaining or increasing device capabilities and maintaining or increasing device end of life as a function of power constraints. The disclosed power regulation circuits, (e.g., device circuit 104 and those additionally described herein) facilitate such goals. For example, an implantable device described herein can have a size that is small enough to be inserted into a human body via a catheter. In an aspect, an implantable device described herein can have dimensions less than or equal to about 19 mm high, 62 mm wide, and 8 mm deep. Such an implantable device can include a pacemaker with full functionality configured to be inserted just beneath the skin of a patient's chest. In another aspect, an implantable device described herein can have a size less than about 1.0 CC. Still in another aspect, an implantable device described herein can have a size from about 0.05 to about 0.1 CC.

FIGS. 1A and 1B depict various non-limiting example locations in the body where an implantable device 100 can be placed. FIG. 1A depicts placement of an implantable medical device in a pectoral region of a person. As shown in FIG. 1B, an implantable device 100 can be placed in a location behind the ear of a patient, particularly the mastoid region. In FIG. 1C, an implantable device 100 is placed in the lower left abdominal region and in FIG. 1D, an implantable device 100 is place in the lower back or upper buttock region of a person. In some aspects, implantable devices described herein can have a size and shape configured to be implanted directly into or around a major bodily organ. For example, implantable device 100 can include a miniature (e.g., less than about 1.0 CC) leadless pacemaker that is implanted directly inside the right ventricular apex of the heart (endocardial) or on the outside of the heart (epicardial).

FIG. 2 illustrates an example implantable device 200 in accordance with aspects described herein. Implantable device 200 includes a housing 202 and a device circuit 204. In various aspects, circuit 204 can include one or more of the structure and/or functionality of circuit 104 (and vice versa). Repetitive descriptions of like elements employed in respective embodiments of circuits described herein are omitted for sake of brevity.

As shown in FIG. 2, device circuit 204 can include one or more power sources 206, a high load power regulator 208, a low load power regulator 210, a regulator switch 212, and one or more internal components 214 that receive power from the one or more power sources 206. The one or more internal components can include high power components 216 configured to receive current from the high load power regulator 208 and one or more low power components 218 configured to receive current from the low load power regulator.

In an embodiment, aspects of device circuit 204 constitute machine-executable components embodied within machine (s), e.g., embodied in one or more computer readable mediums (or media) associated with one or more machines. Such components, when executed by the one or more machines, e.g., computer(s), computing device(s), virtual machine(s), etc. can cause the machine(s) to perform the operations described. According to this embodiment, the internal components 214 include at least a processor (not shown) and a memory (not shown) for storing computer executable components and instructions. The processor can facilitate operation of the computer executable components and instructions by the device circuit 204.

Device circuit 204 employs a power regulation architecture or system configured to regulate power employed by the implantable device 200. The power regulation architecture utilizes a staged power supply approach to only enable a regulator (e.g., either high load power regulator 208 or low load power regulator 210) for a device component 214 function when needed. In particular, circuit 204 includes power circuitry and related components (e.g., regulators 208 and 210 and regulator switch 212) that facilitate providing regulated power to one or more internal components 214 of the implantable device at least as a function of state and associated power requirements of the one or more component 214. By employing the disclosed power regulation circuitry 204, an implantable device that is designed to operate at least in part off of one or more batteries (e.g., device 200 and the like) can conserve overall power consumed over time, ultimately extending device end life. Further, because the range of battery life is extended, the size and/or number of batteries employed by the implantable device can be reduced without having a substantial detrimental effect on device life. As a result, overall size of the implantable device can be reduced.

For example, certain internal components 214 of device 200 can require a higher current to operate than others. The high power components 216 however may not require continuous high power input. In particular, these high power components 216 can be configured to require high power input when in an active state while low or no power input when in a passive state. Rather than supplying high power input to both the high power components 216 and the low power components 218 in a continuous fashion, the power regulation architecture of device circuit 204 can provide low power to the low power components 218 and/or high power components when the high power components are in a passive or off state. The power regulation architecture can further provide high power to the high power components and/or low power components 218 when the high power components are in an active or on state.

In order to provide different current levels to device components 214 as a function of a state (e.g., an active state or a passive state) and/or power requirements of the components 214 (e.g., high power requirements for the high power components 216 and low power requirements for the low power components 218), circuit 204 includes high load power regulator 208, low load power regulator 210 and regulator switch 212. The high load power regulator 208 provides a first current level to device internal components 214 as a function of a first state and associated first power requirements of the device internal components 214. The low load power regulator 210 provides a second current level to device internal components 214 as a function of a second state and associated second power requirements of the device internal components 214, wherein the second current level is lower that the first current level.

The regulator switch 212 switches between operation of the high load power regulator 208 and the low load power regulator 210 as a function a state of the device internal components 214. Accordingly, the regulator switch functions as a multiplexor switch that controls power input from the regulators. In particular, the regulator switch 212 enables power input (e.g., to the device internal components 214) from the high load power regulator 208 and disables power input from the low load power regulator 210 in response to the internal components 214 being in the first state. For example, the first state can be associated with the device high power components 216 being in an active state and the device low power components being in a passive state. The regulator is further configured to disable power input from the high load power regulator 208 and enable power input from the low load power regulator 210 in response to the device internal components being in the second state. For example, the second state can be associated with the device high power components 216 being in an off or passive state and the device low power components also being in a passive state.

In an embodiment, the high load power regulator 208 can provide a high current level to the high power components 216 when the high power components are in an active state or a state otherwise requiring high power input. For instance, the device high power components 216 can include digital components, such as a central processing unit (CPU), that require a high power current when turned on for processing functions and little or no current when in an off or idle state. The high load power regulator 208 can also provide the high current level to the low power components 218 when providing the high current level to the high power components, regardless of state of the low power components 218. In an aspect, the low power components 218 include analog components that function in a continuous passive state whereby low level continuous current is employed to power operation of the low power components 218. For example, low power components can include but are not limited to: a memory/storage component, an oscillator, a clock or a timer, a digital filter, a sensing unit, and another diagnostic data collection unit.

Further, the low load power regulator 210 can provide a low current level to the low power components 218 when the high power components 216 are in an off or idle state. According to this aspect, the low power components can be in a state that requires low current for operation (e.g., a passive state or a low power requiring active state). In an aspect, the low load power regulator 210 can also provide low current level to high power components 216 when providing low current level to low power components 218.

The high load power regulator 208 can be configured to provide various levels of current. In an aspect, the high load power regulator 208 provides current greater than about 15.0 μA. In another aspect, the high load power regulator 208 provides current greater than about 30.0 μA. In another aspect, the high load power regulator 208 provides current greater than about 50.0 μA. In another aspect, the high load power regulator 208 provides current greater than about 75.0 μA. Still in yet another aspect, the high load power regulator 208 provides current up to about 100.0 μA.

The low load power regulator 210 can be configured to provide various levels of current. In an aspect, the low load power regulator 210 provides current less than about 15.0 μA. In another aspect, the low load power regulator 210 provides current less than about 10.0 μA. In another aspect, the low load power regulator 210 provides current less than about 5.0 μA. In another aspect, the low load power regulator 210 provides current less than about 2.0 μA. Still in yet another aspect, the low load power regulator 210 provides current less than about 1.0 μA.

In an aspect, implantable device 200 can include a power regulation system that includes a single regulator, a load capacitor and a filter cap (not shown). According to this aspect, in order to reduce power output by the single power regulator, the power regulation system can increase value of the load capacitor or the filter cap, or reduce current drive of the regulator. However, in another embodiment, as presented in FIG. 2, device circuit 204 can include a power regulation system that includes at least two regulators and a regulator multiplexor switch. By having two regulators, one that is designed to deliver low power at a low current rate (e.g., the low load power regulator 210) and one that is designed to deliver high power at a high current rate (e.g., the high load power regulator 208), the regulation system of device circuit 204 can switch to a higher current rate only when needed. As a result, power consumed by device 200 is reduced.

Further, switching between the high load power regulator 208 and the low load power regulator 210 is controlled by a single regulator switch 212. Accordingly, device circuit 204 employs one set of logic to provide at least two different regulated outputs from which the internal components 214 of the device 200 are powered. Thus, the number of components required by the power regulation aspects of device circuit 204 can be reduced, further attributing to an overall reduction in size of device 200.

Device circuit 204 can include one or more power sources 206 that provide power to the regulators. A power source 206 can include any suitable power source that can provide necessary power for operation of various components of implantable device 200. For example, power source 206 can include but is not limited to a battery, a capacitor, a charge pump, a solar power source, a mechanically derived power source (e.g., MEMs system), or an induction component. In an aspect, power source 206 includes a rechargeable power source. For example, power source 206 can include an induction component configured to receive energy via wireless energy transfer (e.g., using electromagnetic inductance techniques and related components). The received energy can further be employed to provide power to the regulators and/or recharge another power source 206 (e.g., a battery) of the device 200.

In an aspect, device circuit 204 can include a single power source from which the regulators 208 and 210 draw power. In another aspect, device circuit 204 includes at least two power sources, one assigned to the high load power regulator 208 and another assigned to the low load power regulator 210. According to this aspect, the respective power sources can be exclusively employed by the respective regulators to which they are paired or shared between the regulators.

Figure 3:
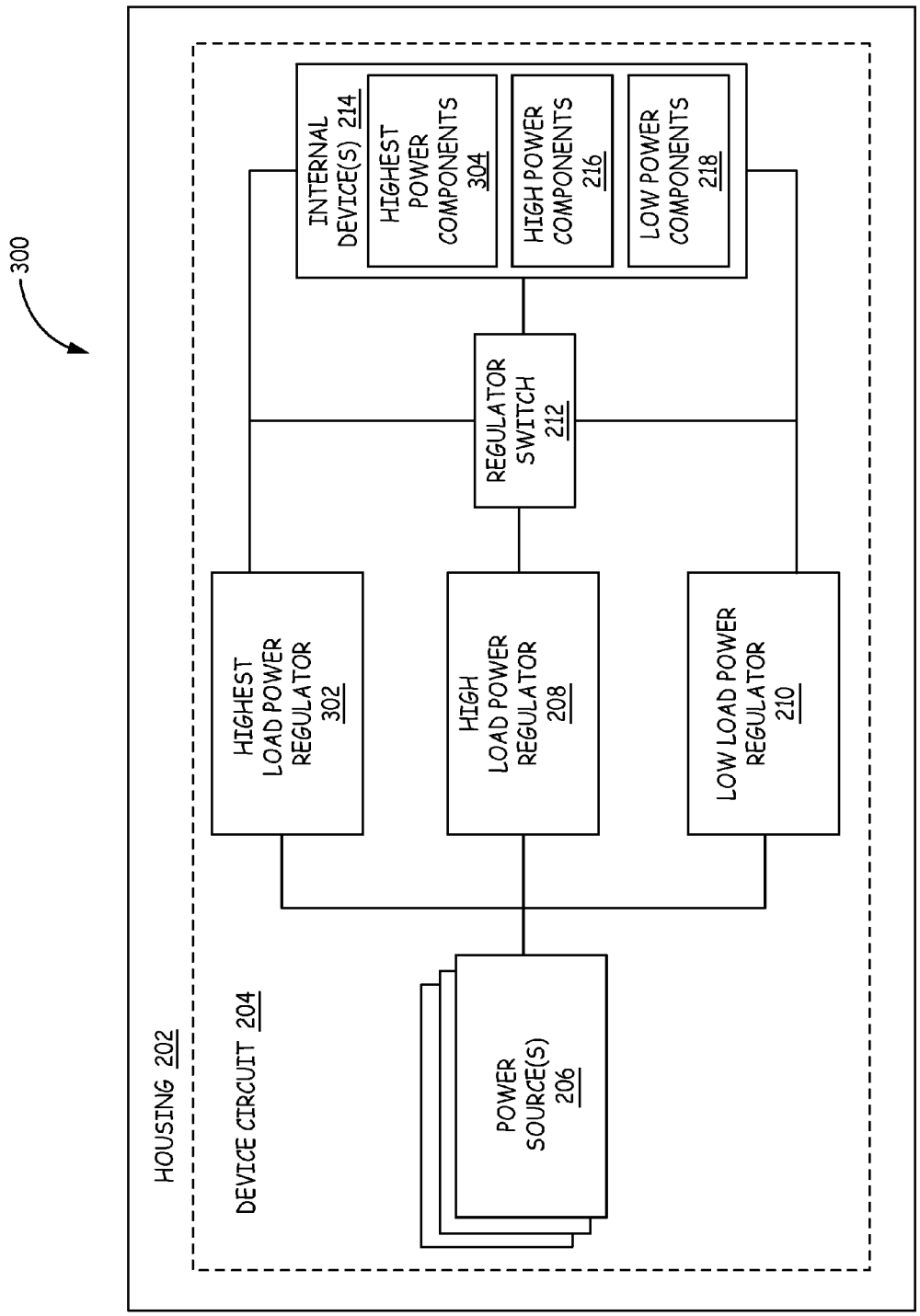
FIG. 3 is an illustration of another example implantable device in accordance with aspects described herein.

FIG. 3 illustrates another example embodiment of an implantable device 300 in accordance with aspects described herein. In various aspects, implantable device 300 can include one or more of the structure and/or functionality of implantable device 200 (and vice versa). Repetitive description of like elements employed in respective embodiments of implantable devices and device circuits described herein are omitted for sake of brevity.

In an aspect, implantable devices described herein can comprise N number of regulators (N is an integer) where each of the N regulators are configured to output different levels of power at different current rates. For example, a plurality of different regulators can be provided within a device power regulation circuit where each of the different regulators are tailored to provide different power levels to device components as a function of respective states and associated power requirements of the components. The regulator switch 212 can further control enablement/disablement of the different regulators such that a single one of the regulators provides current to the one or more of the device components at a time. The plurality of regulators can further employ a single power source or respectively employ a plurality of different power sources 206. With this architecture, where different power levels are needed for different operations of components of the device and the different operations of the components of the device vary over time, only necessary amount of power associated with current device operations can be consumed.

Implantable device 300 presents an example embodiment of a device that employs three regulators to achieve the above noted power consumption effect. Device 300 is similar to device 200 with the addition of a third regulator to the device circuit 204. This third regulator is referred to as the highest load power regulator 302. According to this embodiment, the highest load power regulator 302 is configured to supply a higher current level than the high load power regulator 208 (and consequently a higher current level than the low load power regulator 210 as well). In an aspect, the highest load power regulator 302 is designed to output a high current level for operation of highest power components 304 of device 300. According to this aspect, the highest power components 304 can at times, operate in a state that requires higher power than the high power components 216.

For example, the highest power components 304 can include a flash memory component that requires considerably high amount of power during programming and/or erasing operations. According to this example, in response to receipt of a signal indicating occurrence of a programming operation of the flash memory, the regulator switch can enable power output from the highest load power regulator and disable power output from the high load power regulator 208 and the low load power regulator.

The highest load power regulator 302 can be configured to provide various levels of current. In an aspect, the highest load power regulator 302 provides current greater than about 50.0 $\mu A$. In another aspect, the highest load power regulator 302 provides current greater than about 75.0 $\mu A$. In another aspect, the highest load power regulator 302 provides current greater than about 100.0 $\mu A$. In another aspect, the highest load power regulator 302 provides current greater than about 125.0 $\mu A$. Still in yet another aspect, the highest load power regulator 302 provides current between about 5.0 to about 10.0 mA.

It should be appreciated that the current ranges capable of being supplied by different regulators of power regulation circuits described herein, (e.g., the highest load power regulator 302, the high load power regulator 208, and the low load power regulator 210 respectively) can vary and are not limited to the ranges defined herein. However, the terms high power or high current level and low power or low current level are relative terms. Thus in an aspect, regardless of the current output to which the highest load power regulator 302, the high load power regulator 208 and the low load power regulator 210 are tuned, the highest load power regulator 302 will be tuned to output a current level/rate higher than the high load power regulator 208, and the high load power regulator 208 will be tuned to output a higher current level/rate compared to the current level/rate output by the low load power regulator 210.

Figure 4:
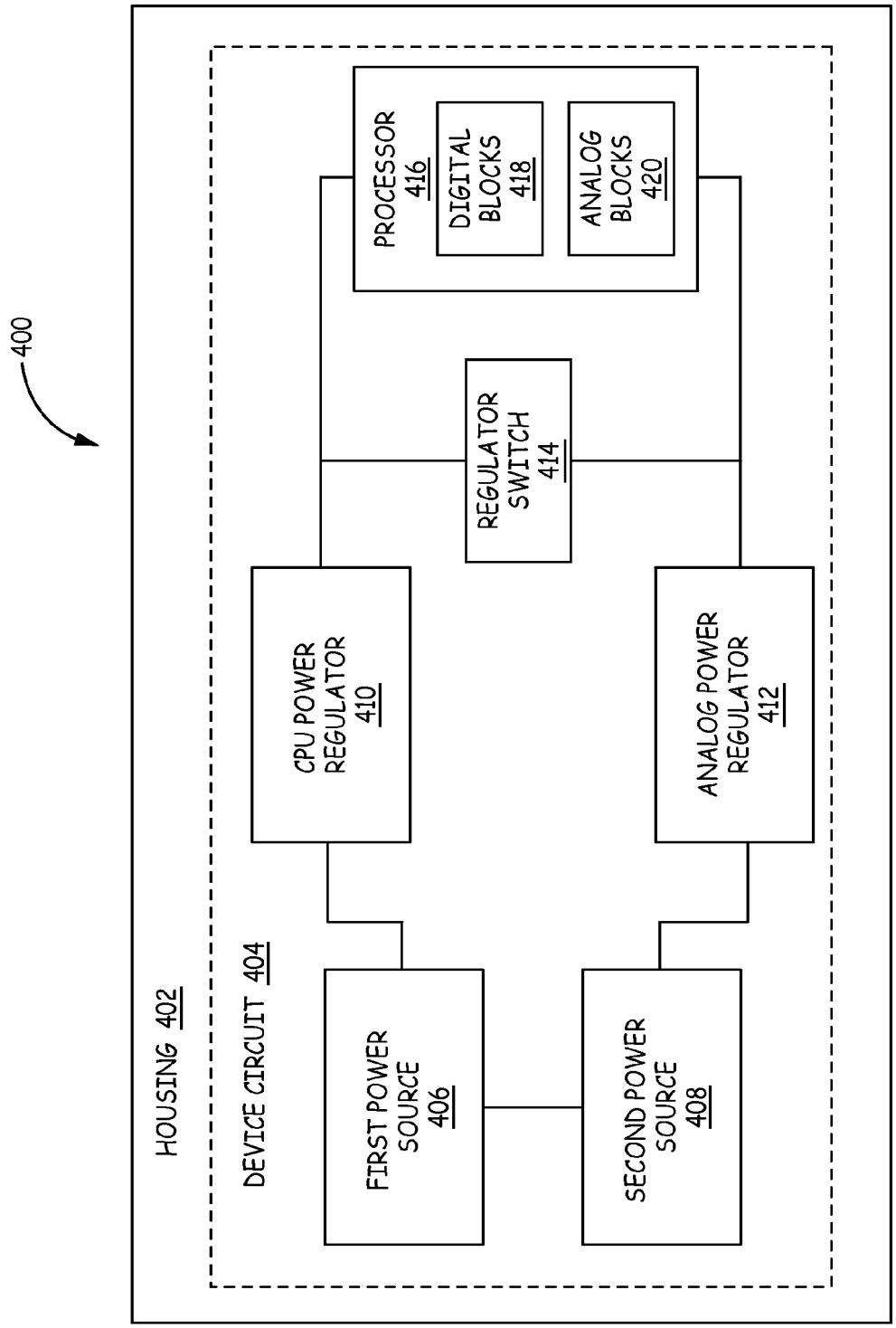
FIG. 4 is an illustration of another example implantable device in accordance with aspects described herein.

Turning now to FIG. 4, presented is another example embodiment of an implantable device 400 in accordance with aspects described herein. In various aspects, implantable device 400 can include one or more of the structure and/or functionality of implantable device 300 (and vice versa). Repetitive description of like elements employed in respective embodiments of implantable devices and device circuits described herein are omitted for sake of brevity.

Implantable device 400 includes a device circuit 404 having power regulation architecture similar to that of device circuit 204. However, in device 400, the device circuit 404 is specifically designed to regulate power provided to digital blocks 418 and analog blocks 420 associated with an internal processor 416 of device 400. According to this embodiment, the device circuit 404 includes a first power source 406, a second power source 408, a CPU power regulator 410, an analog power regulator 412, a regulator switch 414, and a processor 416 including digital blocks 418 and analog blocks. In an aspect, the processor 416 is associated with a non-transitory computer readable medium that stores various computer executable components of device 400.

The CPU power regulator 410 is configured to provide a first current level to processor 416. For example, the CPU power regulator 410 can provide a relatively high current to digital blocks/components 418 of processor 416 when the processor is performing processing operations. The analog power regulator 412 is configured to provide a second current level to the processor, wherein the second current level is lower that the first current level. For example, the analog power regulator 412 can provide a relatively low current to analog blocks/components 420 of processor 416 when the processor is not performing processing operations. The regulator switch 414 is configured to switch power input to the processor between the CPU power regulator 410 and the analog power regulator 412 as a function of a power state, and associated power requirements, of the processor 416.

In an aspect, digital blocks 418 can include components and circuitry involved in processing operations of processor. Analog blocks 420 can include components and circuitry involved in non-processing functions associated with processor 416, such as components involved in sustaining memory (e.g., flash memory components), tracking time (e.g., a clock/timer), or collecting diagnostic data. In an aspect, one or more digital components 418 and/or analog components 420 are located outside of the processor yet operatively coupled to the processor.

In particular, when the processor 416 is turned on for performance of processing operations, the processor employs various digital components/blocks 418 that require relatively higher amount of power than analog components 420. However, when the processor 416 is turned off, small amount of power is needed by the processor to sustain operation of various analog blocks 420. Accordingly, when the processor 416 is turned on for processing functions, the regulator switch 414 is configured to disable power input to the processor via the analog power regulator 412 and enable power input to the processor via CPU power regulator 410. As a result, the CPU power regulator 410 can provide a relatively high current level (e.g., about 50 $\mu A$) to the processor, including the digital blocks 418 (and the analog blocks) when the processor is in an on state. When the processor is in an off or idle state, the regulator switch 414 is configured to disable power output to the processor 416 via the CPU power regulator 410 and enable power output to the processor via the analog power regulator 412. As a result, the analog power regulator 412 can provide relatively low current level (e.g., current less than about $\mu A$) to the processor, including the analog blocks, when the processor is in an off or idle state.

In an aspect, the CPU power regulator 410 regulates power supply for digital components/block 418 of implantable device 400. According to this aspect, the CPU power regulator 410 is considered a digital voltage supply regulator (DVDD). The CPU power regulator 410 can be configured to provide various levels/rates of current. In an aspect, the CPU power regulator 410 provides current greater than about 15.0 μA. In another aspect, the CPU power regulator 410 provides current greater than about 30.0 μA. In another aspect, the CPU power regulator 410 provides current greater than about 50.0 μA. In another aspect, the CPU power regulator 410 provides current greater than about 75.0 μA. Still in yet another aspect, the CPU power regulator 410 provides current up to about 100.0 μA.

In an aspect, the analog power regulator 412 regulates power supply for analog components/blocks 420 of device 400. According to this aspect, the analog power regulator 412 is considered an analog voltage supply regulator (AVDD). The analog power regulator 412 can be configured to provide various levels of current. In an aspect, the analog power regulator 412 provides current less than about 15.0 μA. In another aspect, the analog power regulator 412 provides current less than about 10.0 μA. In another aspect, the analog power regulator 412 provides current less than about 5.0 μA. In another aspect, the analog power regulator 412 provides current less than about 2.0 μA. Still in yet another aspect, the analog power regulator 412 provides current less than about 1.0 μA.

In an aspect, the CPU power regulator 410 is coupled to a first power source 406 from which it draws power and the analog power regulator 412 is coupled to a second power source 408 from which it draws power. According to this aspect, the first power source 406 is dedicated to the CPU power regulator 410 and the second power source 408 is dedicated to the analog power regulator 412. The first power source 406 and the second power source can include one or more of the power sources discussed with reference to power sources 206. In an aspect, the first power source 406 is a battery while the second power source includes one or more capacitors and a charge pump/down converter that draw power from another battery. In another aspect, the first power source 406 and the second power source 408 can share power. For example, the first power source 406 can transfer power to the second power source 408 and vice versa.

The CPU power regulator 410 and analog power regulator 412 scheme of device circuit 404 can be employed by an implantable device 400 to conserve power. In particular, with the subject power regulation scheme, device components consume only a required amount of power when operating. Further, the subject power regulation scheme mitigates current drain associated with regulator power draw. For example, when the CPU power regulator 410 is operatively coupled to the processor 416, when the processor 416 is in an off state, there is excess leakage current between the CPU power regulator 410 and the processor as a result of the CPU power regulator being on. By turning off the CPU power regulator 410 when the processor is in an off or idle state, current draw can be minimized or eliminated. This operation allows the device circuit 404 to save the regulator current drain which can be significant due to small component values being used as hold caps. For example, where an average current drain associated with a CPU regulator being on when the CPU is not in operation is about 1.0 μA, the gain in saved current is about 1.0 μA.

The power regulation scheme of device circuit 404 is particularly well suited for devices that include one or more internal components that do not require constant load, such as devices that apply a standby current to internal components a majority of the time (e.g., 90% or greater). As used herein, the term duty cycle refers to the amount of time a high power requiring component (e.g., digital blocks 418 associated with processing operations), relative to a low power requiring component, (e.g., analog blocks 420 associated with maintaining memory) of a device is in an active state compared to the amount of time the high power requiring component is in an off or passive state. In particular, implantable medical devices, such as device 400, that are event driven (e.g., an occurrence of an irregular heart beat) have relatively low duty cycles (e.g., less than 10%). Accordingly, the digital blocks 418 only require relatively high power input a relatively low fraction of the time (e.g., less than 10%). In an aspect, device 400 has a CPU duty cycle of less than about 10.0%. In another aspect, device 400 has a CPU duty cycle of less than about 5.0%. Still in yet another aspect, device 400 has a CPU duty cycle less than about 1.0%. Still another aspect, device 400 has a CPU duty cycle from about 0.1% to about 5.0%.

In an example, device 400 has a CPU duty cycle of less than about 3% (e.g., the processor is in an active state less than 3% of the time). A 3% CPU duty cycle equates to a CPU on time of a few milliseconds (e.g., about 25 to about 35 ms) every few seconds (e.g., about every 1 to 3 seconds). With a duty cycle of less than about 3%, device 400 can reduce the average amount of current drain associated with the CPU power regulator to about 30.0 nA when using the power regulation scheme of circuit 404. For example, without the power regulation scheme of circuit 404, an implantable device similar to device 400 with a duty cycle less than about 3% would have an average amount of current drain associated with the CPU power regulator of about 1000.0 nA. Accordingly, device 400 can achieve significant power savings over time resulting in extended device longevity.

In an aspect, the regulator switch 414 can have a disabling function whereby it directs hardware associated with the CPU power regulator to disable the current drain from the analog power regulator 412 and switch the standby digital leakage current onto the analog power regulator 412. The regulator switch 414 can then switch on the analog power regulator 412 so that when the processor is in an off or passive state, current is provided to the processor 416 via the analog power supply. When an event is received and requires the processor 416 to be enabled, the CPU power regulator becomes active and the regulator switch 414 switches the CPU regulator on. The CPU power regulator 410 can then provide high power to the processor 416.

Figure 5:
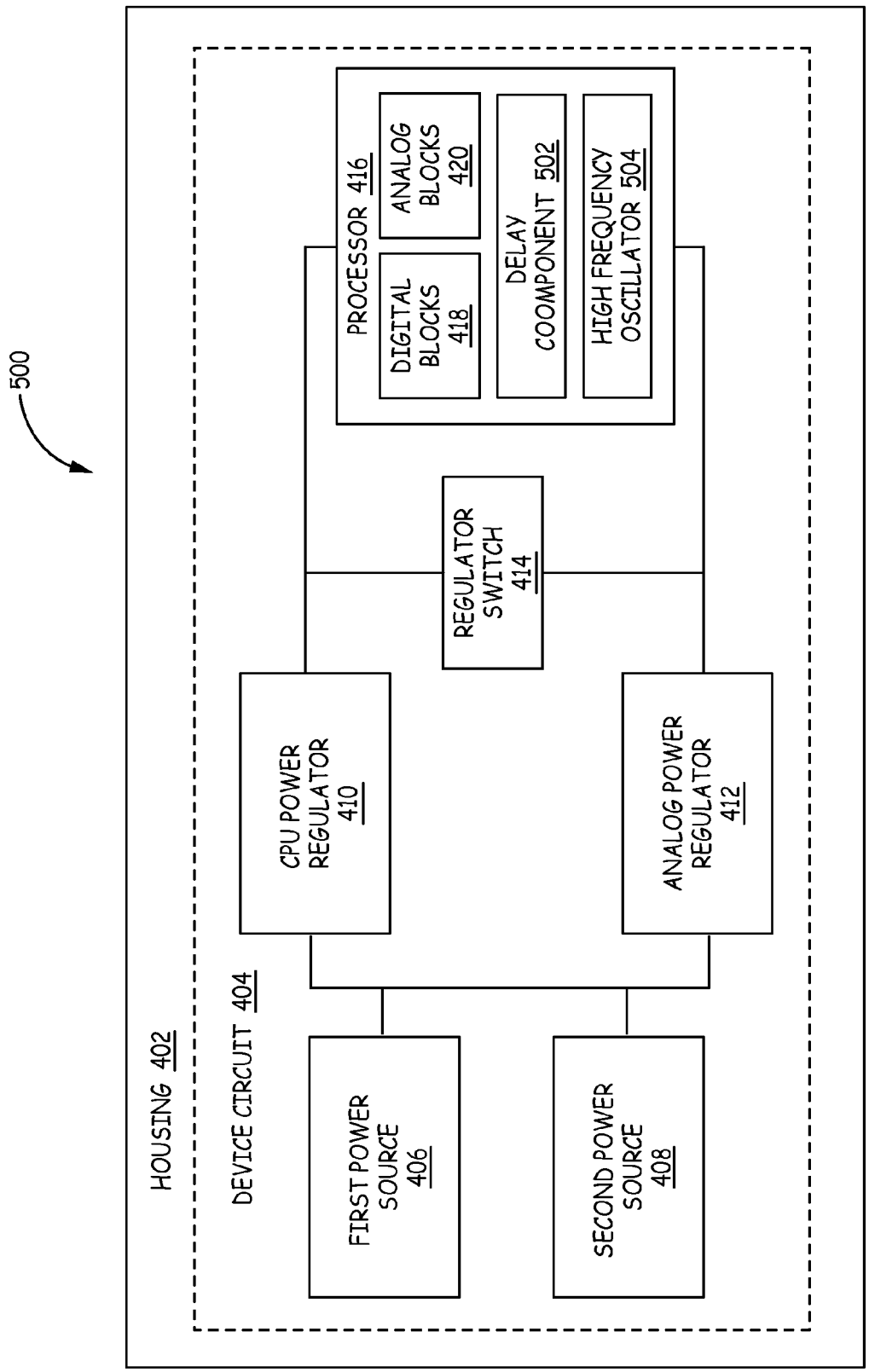
FIG. 5 is an illustration of another example implantable device in accordance with aspects described herein.

With reference now to FIG. 5, presented is another example embodiment of an implantable device 500 in accordance with aspects described herein. In various aspects, implantable device 500 can include one or more of the structure and/or functionality of implantable device 400 (and vice versa). Repetitive description of like elements employed in respective embodiments of implantable devices and device circuits described herein are omitted for sake of brevity.

Implantable device 500 is similar to implantable device 400 with the addition of delay component 502 and high frequency oscillator 504 to processor 416. In an aspect, although the delay component 502 and the high frequency oscillator 504 are depicted as being included with processor 416, these components can be located externally from processor 416. For example, one or more of the delay component 502 or the high frequency oscillator 504 can be located externally to processor 416 and operatively coupled to the processor via circuitry 404. In another example, one or more of the delay component 502 or the high frequency oscillator 504 can be located within the regulator switch 414.

The delay component 502 is configured to provide a delay to digital operation of the processor (e.g., active state operation of the digital blocks 418 of the processor) to allow the CPU power regulator 410 to become stable prior to providing current to the processor. For example, in response to receipt of a signal indicating an event that requires the processor to be turned on, the CPU power regulator 410 is configured to turn on and warm up/stabilize before the digital operation of the processor is turned on. The delay component 502 is configured to effect a delay to digital operation of the processor to allow the CPU power regulator 510 to warm up/stabilize. Then, after the CPU power regulator 410 stabilizes, the regulator switch 414 can enable current draw from the CPU power regulator 410.

The delay period effected by the delay component 502 can vary. In an aspect, the delay period is less than about 10.0 milliseconds. In another aspect, the delay period is less than about 5.0 milliseconds. In another aspect, the delay period is less than about 2.0 milliseconds. Still in yet another aspect, the delay period is less than about 1.0 milliseconds.

The high frequency oscillator 504 facilitates turning on and stabilization of the CPU power regulator 410 as well as turning off of the CPU power regulator 410. In particular, the high frequency oscillator 504 is configured to provide a first dynamic current to the CPU power regulator 410 in response to the initial turning on of the CPU power regulator 410 based on a trigger event. This first dynamic current is the first current seen by the CPU power regulator 410 at this time. Once the CPU power regulator 410 is stabilized/warmed up and waiting to support the high peak current needed for processing operations of the processor 416, the digital operation of the processor is turned on and the regulator switch 414 opens the switch to the CPU power regulator 410, allowing influx of the high current generated by the CPU power regulator 410. After the processor signals the event requiring digital operation of the processor 416 is complete, the processor 416 can shutdown the high frequency oscillator 504 which in turn signals the CPU power regulator 410 to turn off. At this time, the regulator switch 414 can disable power input via the CPU power regulator 410 and enable power input via the analog power regulator 412.

Figure 6:
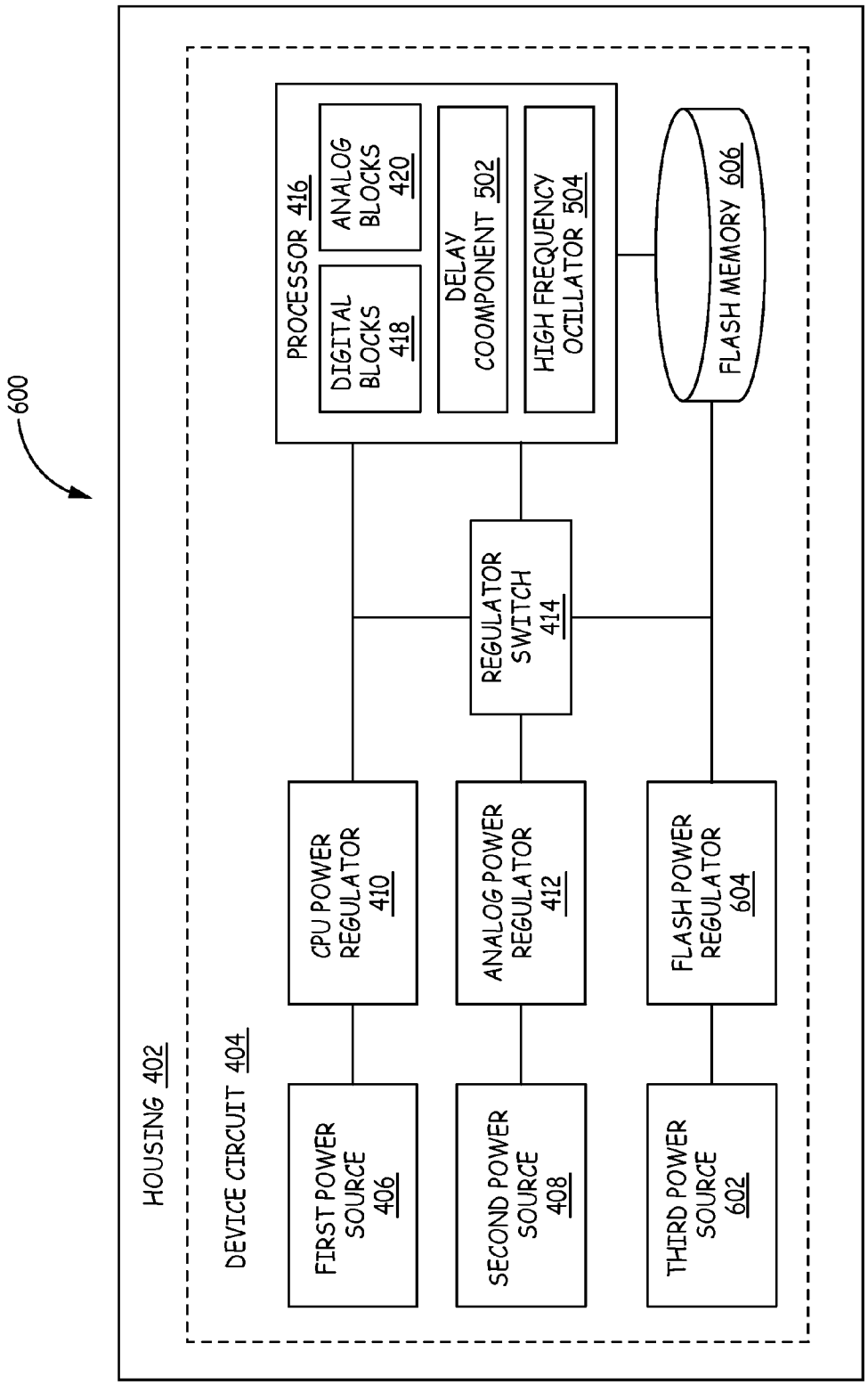
FIG. 6 is an illustration of another example implantable device in accordance with aspects described herein.

With reference to FIG. 6, presented is another example embodiment of an implantable device 600 in accordance with aspects described herein. In various aspects, implantable device 600 can include one or more of the structure and/or functionality of implantable device 500 (and vice versa). Repetitive description of like elements employed in respective embodiments of implantable devices and device circuits described herein are omitted for sake of brevity.

Implantable device 600 is similar to implantable device 500 with the addition of a third regulator, flash regulator 604, a third power source 602 and flash memory 606 to device circuit 404. Flash memory is an electronic non-volatile computer storage device that can be electrically erased and reprogrammed. Programming and/or erasing functions associated with flash memory typically require a much higher current than CPU operation and are less frequently performed. Device circuit 404 can operate in a similar fashion to device circuit 204 described with reference to FIG. 3. In this respect, the flash regulator 604 can be likened to the highest load power regulator 302, the CPU power regulator 410 can be likened to the high load power regulator 208, and the analog power regulator can be likened to the low load power regulator 210.

According to this embodiment, the flash regulator 604 is configured to supply a higher current level than CPU power regulator 410 for programming and/or erasing operations of the flash memory 606. In an aspect, in response to receipt of a signal indicating occurrence of a programming operation of the flash memory 606, the regulator switch 414 can enable power output from the flash regulator 604 and disable power output from the CPU power regulator 410 and the analog power regulator 412. The flash regulator 604 can further draw power directly from a third power source 602.

The flash regulator 604 can be configured to provide various levels of current for programming and/or erasing operations associated with the flash memory. The flash regulator 604 is also configured to increase the voltage it supplies to support a flash operation. Accordingly, the flash regulator is both dynamic in current loads and voltage levels.

In an aspect, the flash regulator 604 provides current greater than about 0.05 mA. In another aspect, the flash regulator 604 provides current greater than about 0.1 mA. In another aspect, the flash regulator 604 provides current greater than about 0.5 mA. In another aspect, the flash regulator 604 provides current greater than about 1.0 mA. Still in yet another aspect, the flash regulator 604 provides current less than about 2.1 µA.

Figure 7A:
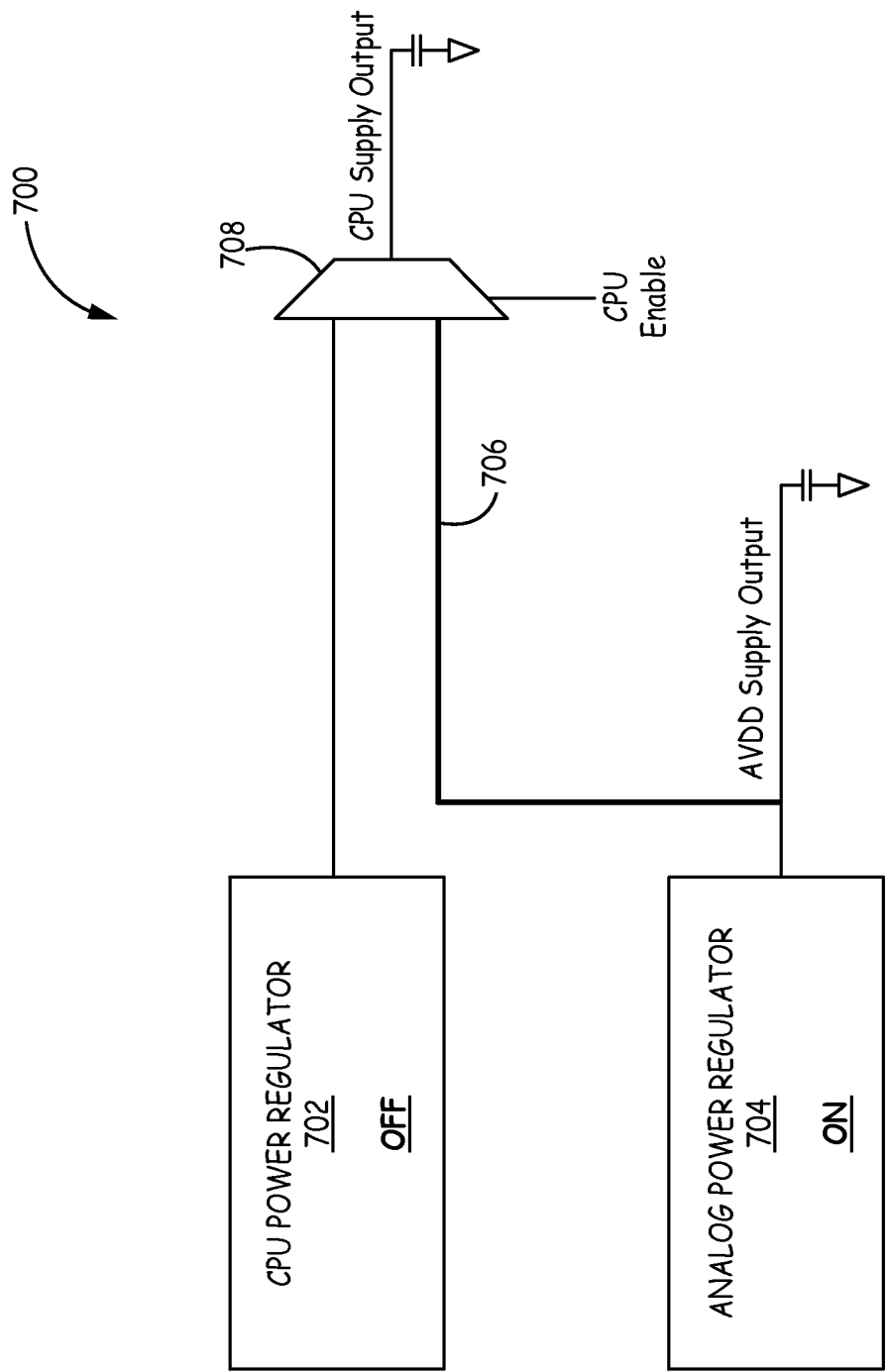
FIG. 7A demonstrates operation of power regulation circuitry when a central processing unit (CPU) powered via the circuitry is in an off state in accordance with aspects described herein.
Figure 7B:
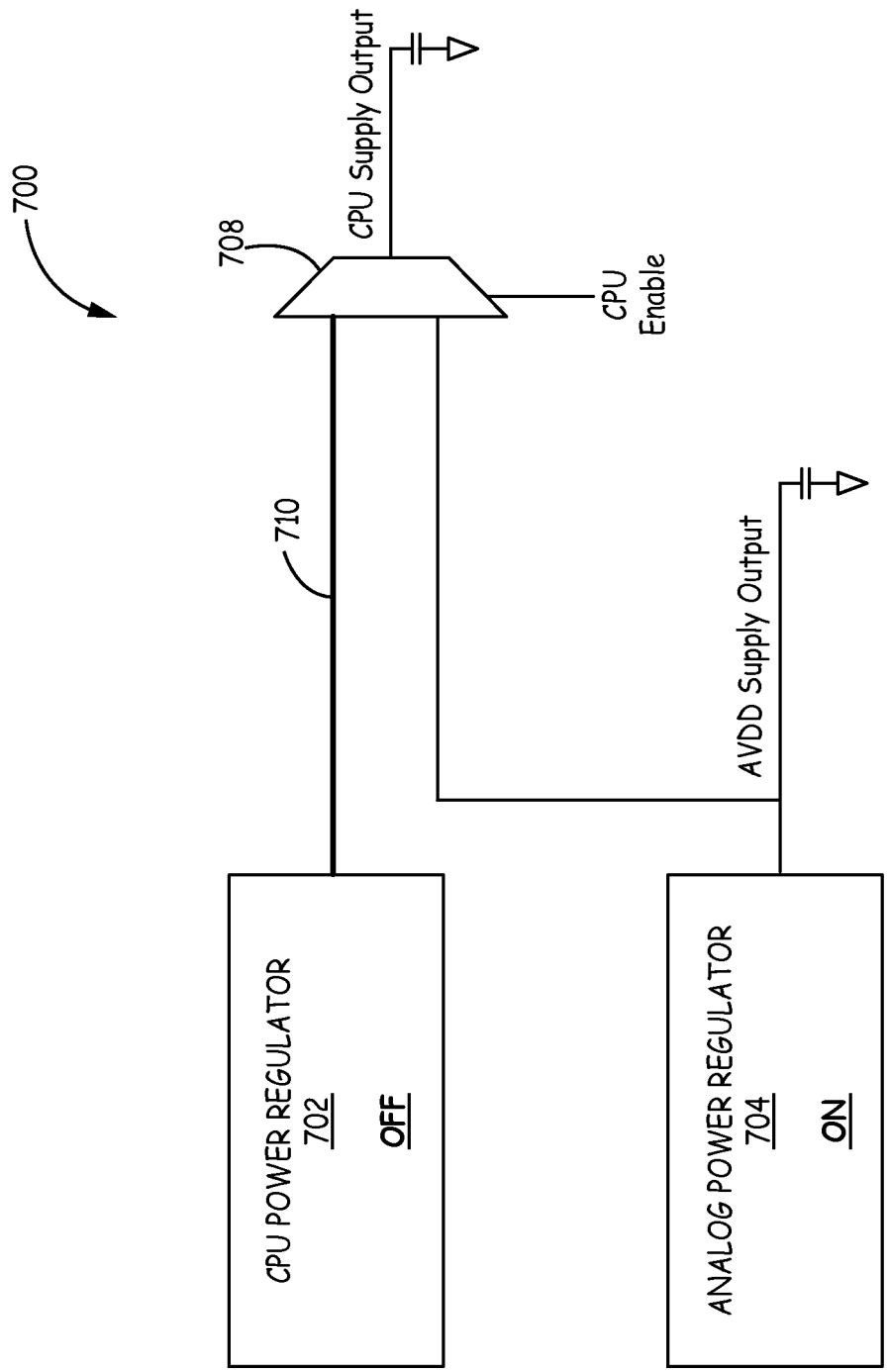
FIG. 7B demonstrates operation of power regulation circuitry when a CPU powered via the circuitry is in an on state in accordance with aspects described herein.

FIGS. 7A-7B, present example embodiments of a power regulation circuit 700 capable of being employed by an implantable device as described herein. Repetitive description of like elements employed in respective embodiments of implantable devices and implantable device circuits described herein are omitted for sake of brevity.

Circuit 700 includes a CPU power regulator 702, an analog power regulator 704 and regulator switch 708. The CPU power regulator 702 provides high current output for active CPU operations. In an aspect, the CPU power regulator 702 provides a current between about 10.0 uA and about 50.0 uA. In order to provide a relatively high current, the CPU power regulator 702 also consumes power in the range of about 1.0 uA. The analog power regulator 704 provides low current output for low current requiring components (e.g., memory or a timer) of an implantable device. In an aspect, the analog power regulator 704 provides up to 10.0 uA of power to various low power analog circuit components. The analog power regulator 704 will also consume current in the range of 100.0 nA.

FIG. 7A demonstrates operation of the power regulation circuitry 700 when a CPU (not shown) powered via the circuitry is in an off state. When the CPU is turned off (e.g., when digital components of the CPU are turned off), the circuit 700 will only draw leakage current from the CPU supply output (which is less than about 1.0 uA). At this time the CPU power regulator 702 is turned OFF to save current while the analog power regulator 704 is turned ON. The regulator switch 708 is implemented to connect the analog power regulator 704 for supplying the CPU supply output for the CPU analog components when the CPU operation is in an OFF state. The bolded line 706 highlights the path where the CPU supply output is being provided by the analog power regulator 704.

FIG. 7B demonstrates operation of the power regulation circuitry 700 when the CPU (e.g., particularly the digital components of the CPU) powered via the circuitry is in an on state. At this time the CPU power regulator 702 is turned ON while the analog power regulator 704 is turned OFF. The regulator switch 708 is implemented to connect the CPU power regulator 702 for supplying the CPU supply output for the CPU digital components when the CPU operation is in an ON state. The bolded line 710 highlights the path where CPU supply output is being provided by the CPU power regulator 702.

Figure 8:
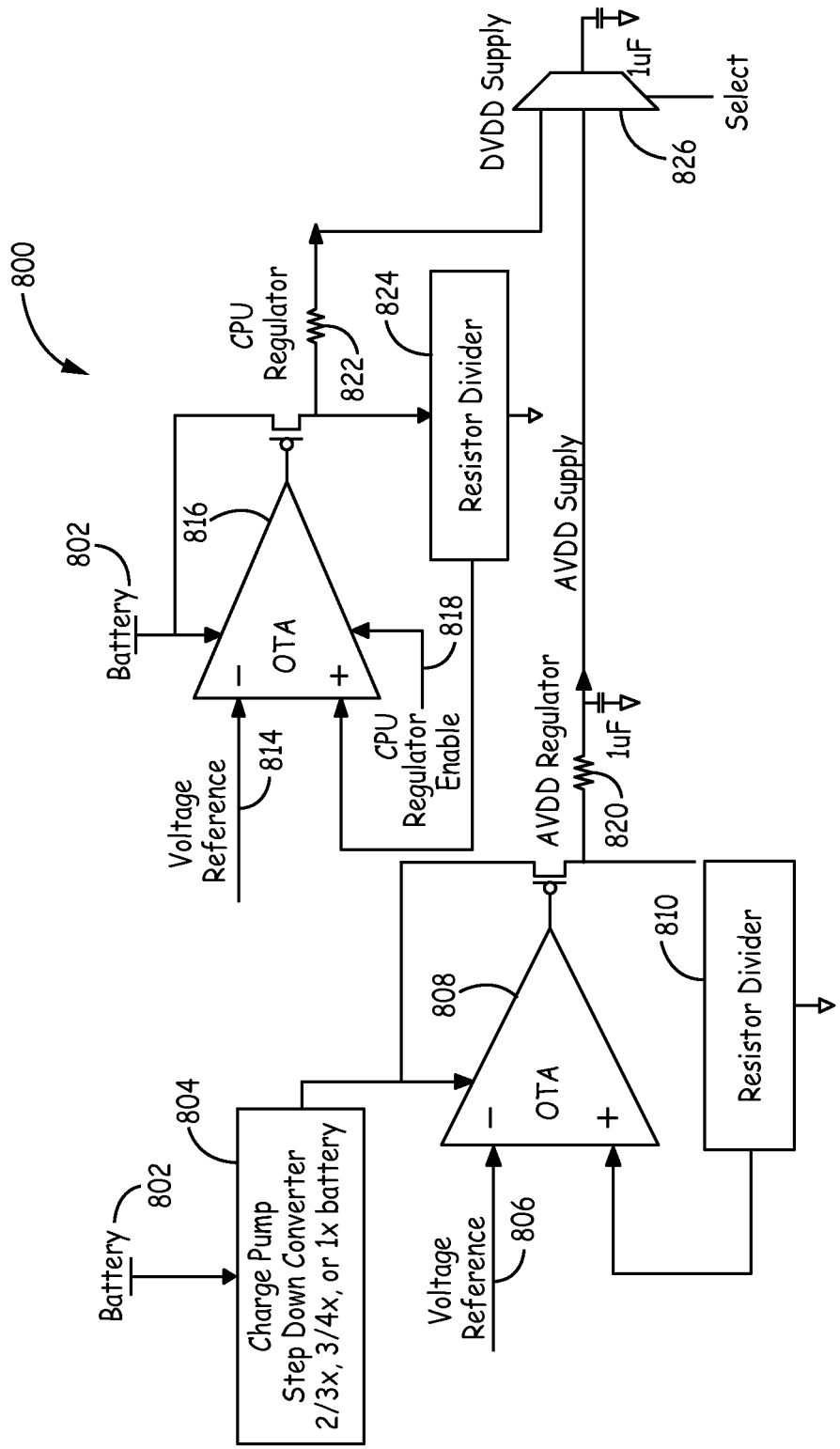
FIG. 8 presents an example embodiment of a power regulation circuit capable of being employed by an implantable device in accordance with aspects described herein.

Turning now to FIG. 8, presented is another example embodiment of a power regulation circuit 800 capable of being employed by an implantable device as described herein. Repetitive description of like elements employed in respective embodiments of implantable devices and implantable device circuits described herein are omitted for sake of brevity.

Circuit 800 includes an analog voltage (AVDD) regulator 820 configured to output an AVDD supply, and a CPU regulator 822 configured to output a digital voltage regulator (DVDD) supply. The circuit 800 further includes a regulator switch 826, such as a multiplexor, that is configured to selectively enable and disable the AVDD regulator 820 and the CPU regulator 822 at least as a function of a state and associated power requirements of one or more device components being supplied power via circuitry 800. In an example embodiment, circuit 800 is configured to provide power to a CPU (not shown) associated with analog and digital components.

In an aspect, as seen in circuit 800, the AVDD regulator 820 is powered via battery, 802. The AVDD regulator 820 is associated with various circuit elements that facilitate operation of the AVDD regulator 820, including a charge pump/step down converter 804, an operational transconductance amplifier (OTA) 808 that receives a reference voltage 806, and a resistor divider 810. The CPU regulator 822 is also powered via battery 802. In an aspect, (although not depicted in this manner), the AVDD regulator 820 and the CPU regulator 822 can employ separate power sources. The CPU regulator 822 is also associated with various circuit elements similar to those employed by the AVDD regulator, including an OTA 816 that receives a reference voltage 814 and a CPU regulator enable/disable signal 818, and a resistor divider 824.

In an example embodiment, circuit 800 is employed in an implantable device that has a relatively low duty cycle (e.g., less than 10%). Therefore, for a majority of the time, the CPU being powered via the circuit 800 is in an off or idle state. When the CPU is in an off or idle state, the CPU regulator 822 is turned off (e.g., via the regulator switch 826) and the charge pump/step down converter 804 provides current to the AVDD regulator 820 which powers low current analog circuitry of the disabled CPU and/or other analog components associated with the implantable device. The analog circuitry of the disabled CPU and/or other analog components associated with the implantable device consume less than about 1.0 μA from the AVDD supply. The AVDD regulator 820 is designed for extremely low current drain (e.g., about 0.1 uA) and has relatively high output impedance (e.g., about 1500 Ohms) and low output current capability (e.g., about 10.0 uA). The charge pump/step down converter 804 enables the current from the battery 802 to be a fraction (e.g., ⅔, ¾ or 1×) of the current out of the AVDD regulator 820.

When the CPU is turned on, (e.g., in response to a trigger event or a programmed schedule) the CPU regulator 822 is turned on (e.g., via the regulator switch 826) and the AVDD regulator 820 is turned off. In an aspect, prior to turning on the CPU, the CPU regulator 822 is turned on and allowed to stabilize while the multiplexor switch to AVDD regulator is kept open and the regulator switch 826 to the CPU regulator is kept closed. The CPU regulator 822 has a lower output impedance (e.g., approximately 100.0 Ohms) than the AVDD regulator 820 and can provide more current to power the CPU (e.g., up to 100.0 uA).

In an aspect, the CPU regulator 822 is power directly from battery 802. In particular, the CPU regulator 822 consumes considerably more current (e.g., about 1.0 uA) than the AVDD regulator 820 and can be powered directly from battery 802, 812 to prevent overloading the charge pump/step down converter 804 and impacting the output of the AVDD regulator 820. However, where the CPU duty cycle is low (e.g., from about 0.1% to about 5.0% for example) the average current received at the CPU is extremely low. Thus it is not essential to provide the for the CPU regulator via a charge pump/step down converter 804. For example, an implantable medical device that employs a CPU in an on mode for a few milliseconds (e.g., about 30 ms) every few seconds (e.g., about every 1-2 seconds) may have a duty cycle of about 0.1% to about 0.2%. According to this example, the average current received by the CPU is about 0.05 to about 0.1 uA.

In another aspect, the CPU regulator 822 can be powered via a charge pump, such as charge pump/step down converter 804. According to this aspect, the CPU regulator 822 and the AVDD regulator can share battery 802 and charge pump/step down converter 804. For example, as the CPU duty cycle increases, the average CPU current can represent a considerable portion of the total current drain. Thus operating the CPU regulator from a charge pump can be beneficial.

The output voltages for the AVDD regulator 820 and the CPU regulator 822 are set by the voltage reference values 806 and 814 and resistor divider ratios associated with resistor divider 810 and resister divider 824, respectively. In an aspect, the output voltages of for the AVDD regulator 820 and the CPU regulator 822 are different. In another aspect, the output voltages of the AVDD regulator 820 and the CPU regulator 822 are the same or substantially the same. In an example, the output voltage value of the two regulators 820 and 822 is about 1.5 V to about 2.0 V. According to this example, the voltage reference values 806 and 814 are approximately set to 1.2 V, regardless of whether the CPU is on or not.

In another aspect, where the AVDD regulator 820 and the CPU regulator 822 have the same or substantially the same output voltage, circuit 800 can eliminate the resistor divider 824 for the CPU regulator 822 and use the AVDD output voltage as a reference. In such a scenario (not shown), the output voltage of the AVDD regulator 820 can tie directly to the input of the OTA 816 rather than being attenuated by the resistor divider 824.

Figure 9:
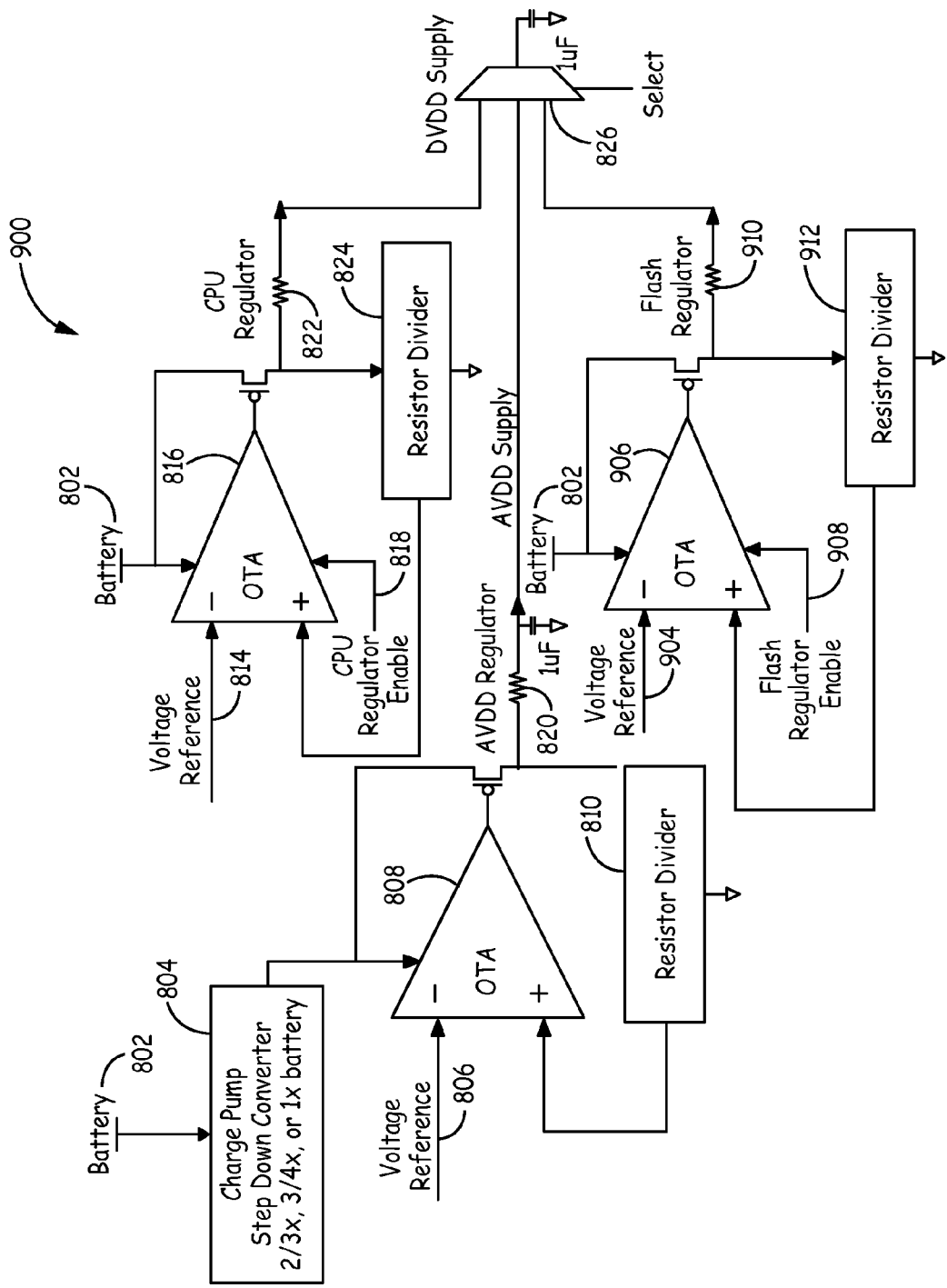
FIG. 9 presents another example embodiment of a power regulation circuit capable of being employed by an implantable device in accordance with aspects described herein.

Turning now to FIG. 9, presented is another example embodiment of a power regulation circuit 900 capable of being employed by an implantable device as described herein. Repetitive description of like elements employed in respective embodiments of implantable devices and implantable device circuits described herein are omitted for sake of brevity.

Circuit 900 is similar to circuit 900 with the addition of a third regulator, flash regulator 910. Flash regulator 910 is configured to provide power to a flash memory component (e.g., a non-volatile memory storage component) of a device in which circuit 900 is employed. In an aspect, the flash memory component is included in or otherwise operatively coupled to, a CPU of the device. The flash regulator 910 is also associated with various circuit elements similar to those employed by the CPU regulator 922, including an OTA 906 that receives a reference voltage 904 and a flash regulator enable/disable signal 908, and a resistor divider 912.

The flash regulator 910 is configured to provide a higher current than the CPU regulator 822 to flash memory during programming and/or erasing operations. In an aspect, the regulator switch 926 can turn the flash regulator 910 on only in response to programming and/or erasing operations. At times when programming/erasing is not being performed, the regulator switch 926 can close off input from the flash regulator 910. For example, when the CPU is in an off state, the regulator switch 926 can close off a switch that allows power input from the flash regulator 910, essentially turning the flash regulator off.

In an aspect, prior to flash memory program or erase, the flash regulator 910 is turned on and allowed to stabilize. The flash regulator has a lower output impedance (e.g., about 10.0 Ohms) than the CPU regulator 822 and can provide more current to power the flash memory during programming/erasing (e.g., about 2.0 mA). The flash regulator 910 further consumes substantially more power than the CPU regulator 822 (e.g., about 20 uA) and is powered directly from a battery 802 to prevent overloading the charge pump/step down converter 804 and AVDD regulator 820.

In some aspects, during flash program and erase, the CPU regulator 822 voltage can increase. For example, as noted above, in general a 1.7V is used on the AVDD regulator 820 supply, a 1.7V for the CPU regulator 822 regulator supply, and 2V for the flash regulator 910 supply. However, at times during flash program and erase the CPU regulator 822 supply can be increased to 2V. Accordingly, when programming flash memory (which happens very rarely), system 900 can increase the CPU regulator 822 voltage to 2V to power the CPU and the flash memory to insure the write/erase function will work without affecting the 1.7V operation of the analog circuitry. When system 900 is merely enabling the CPU and reading from flash memory, system 100 can use the 1.7V on the CPU regulator 822 since peak current and voltage demands are lower.

In various aspects, the voltage regulators (e.g., regulators 820, 822, and 910) of the disclosed power regulation schemes are configured to have strong pull up current capability and weak pull down capability. This helps avoid contention if there are timing issues with opening/closing switches when connecting two voltage regulators with slightly different voltages. According to this aspect, whichever voltage output is higher controls the output voltage when two regulators are momentarily connected without causing excessive current drain. For example, if the CPU regulator 822 is enabled while the switch between the CPU regulator 822 and the AVDD regulator 820 is closed, the voltage will rise to the greater of the two voltages but will not result in excessive battery current drain. Similarly, if the switch between the CPU regulator 822 and the AVDD regulator 820 is closed before the CPU regulator is disabled, there will not be contention.

Figure 10:
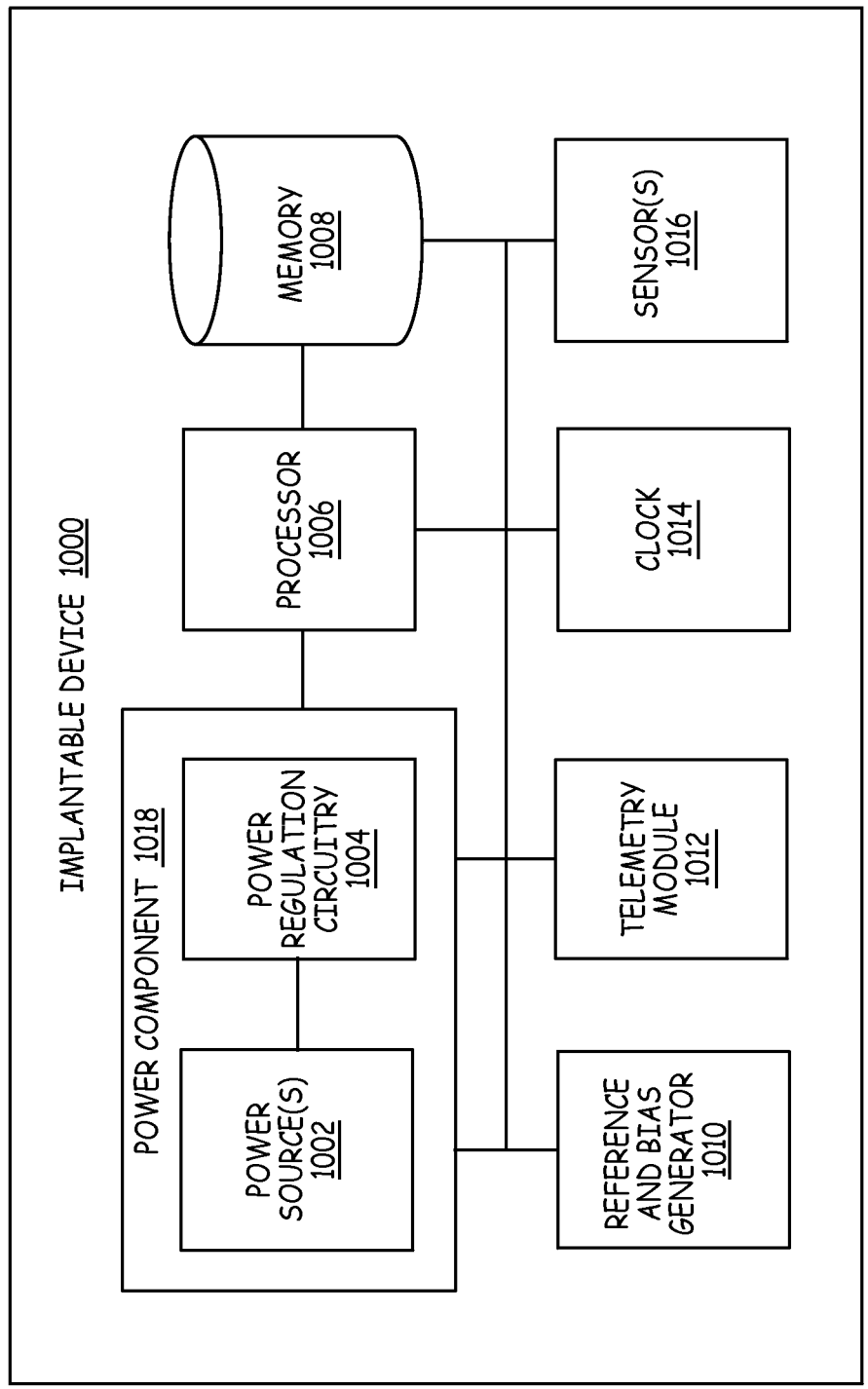
FIG. 10 is an illustration of an example implantable device employing power regulation circuitry in accordance with aspects described herein.

FIG. 10 presents a high level embodiment of an example implantable device 1000 capable of employing the disclosed power regulation circuitry to facilitate conserving power. In various aspects, device 1000 can include one or more of the structure and/or functionality of devices 100-600 described herein. Repetitive description of like elements employed in respective embodiments of implantable devices and circuits described herein are omitted for sake of brevity.

Implantable device 1000 can include power component 1018 that includes one or more power sources 1002 and power regulation circuitry 1004. The power component 1018 can embody the power regulation systems/schemes disclosed herein. In particular, the one or more power sources can include any of the power sources discussed with respect to power sources 206 and the power regulation circuitry can include one or more of the aspects of the various device circuitry described herein (e.g., including a plurality of regulators and a regulator switch).

The implantable device can further include a processor 1006, memory 1008, and one or more additional digital and/or analog components, including but not limited to a reference and bias generator 1010, a telemetry module 1012, a clock/timer, and one or more sensors 1016. The implantable device 1000 is configured to operate using the power component 1018 to provide power to and regulate power consumption by the plurality of device components (e.g., the processor 1006, the memory 1008, the reference and bias generator 1010, the telemetry module 1012, the clock 1014 and the one or more sensors).

FIGS. 11-14 illustrates methodologies or flow diagrams in accordance with certain aspects of this disclosure. While, for purposes of simplicity of explanation, the methodologies are shown and described as a series of acts, the disclosed subject matter is not limited by the order of acts, as some acts can occur in different orders and/or concurrently with other acts from that shown and described herein. For example, those skilled in the art will understand and appreciate that a methodology can alternatively be represented as a series of interrelated states or events, such as in a state diagram. Moreover, not all illustrated acts may be required to implement a methodology in accordance with the disclosed subject matter. Additionally, it is to be appreciated that the methodologies disclosed in this disclosure are capable of being stored on an article of manufacture to facilitate transporting and transferring such methodologies to computers or other computing devices.

Figure 11:
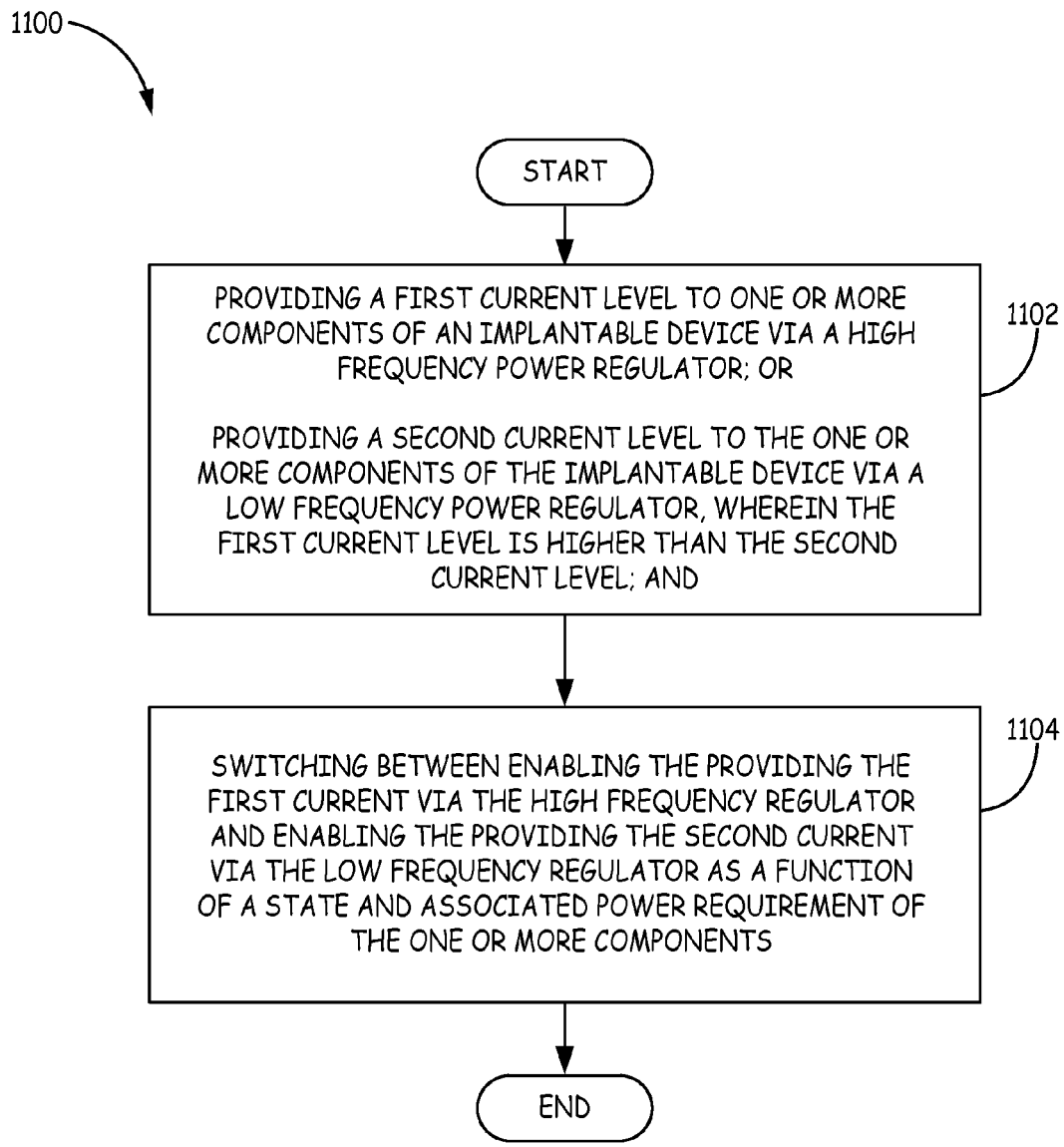
FIG. 11 illustrates an example methodology for regulating power consumption of an implantable device in accordance with aspects described herein.

Referring now to FIG. 11, presented is a flow diagram of an example application of systems and apparatuses disclosed in this description in accordance with an embodiment. In an aspect, in exemplary methodology 1100, an implantable device (e.g., device 100 and the like) employs a power regulation circuit, such as those described herein, to facilitate regulating power consumed during operation of the device. At 1102, either a first current level is provided to one or more components of an implantable device via a high load power regulator or a second current level is provided to the one or more components of the implantable device via a low load power regulator, wherein the first current level is higher than the second current level. At 1102, a regulator switch (e.g., regulator switch 212 and the like) switches between enabling the providing the first current level via the high frequency power component and enabling the providing the second current via the low frequency power component as a function of a state and associated power requirement of the one or more components.

Figure 12:
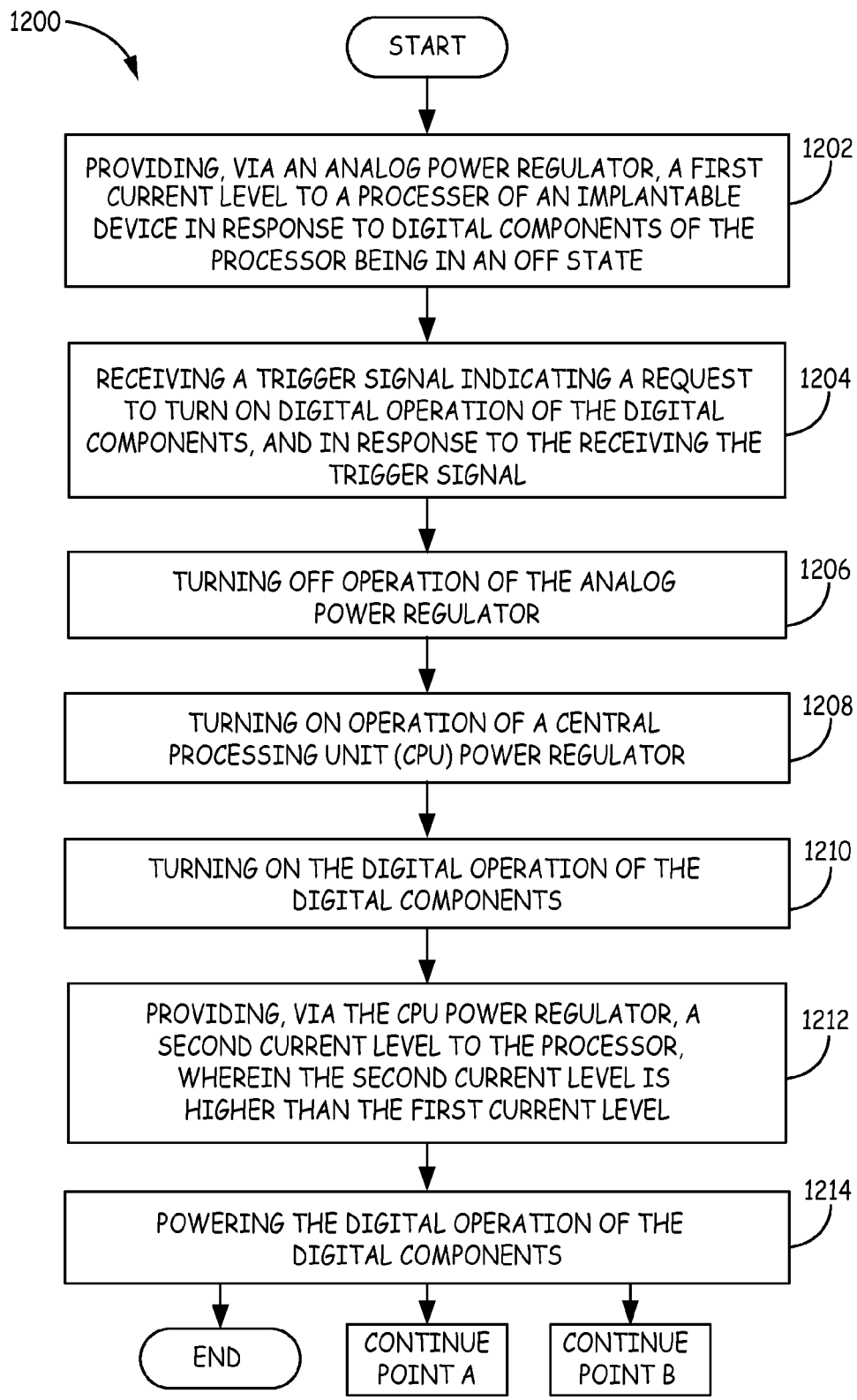
FIG. 12 illustrates another example methodology for regulating power consumption of an implantable device in accordance with aspects described herein.

Turning now to FIG. 12, presented is another method 1200 for regulating power consumption of an implantable device. Methodology 1200 can continue on at continue point A and/or continue point B as described with reference to methods 1300 and 1400 respectively, discussed infra. At 1202, a first current level is provided, via an analog power regulator, to a processer of an implantable device in response to digital components of the processor being in an off state. At 1204, a trigger signal indicating a request to turn on digital operation of the digital components is received. In response to receiving the trigger signal, acts 1206-1214 are performed. At 1206, operation of the analog power regulator is turned off. At 1208, operation of a central processing unit (CPU) power regulator is turned on. At 1210, the digital operation of the digital components is turned on. At 1212, a second current level is provided to the processor via the CPU power regulator, wherein the second current level is higher than the first current level, and at 1214, the digital operation of the digital components is powered.

Figure 13:
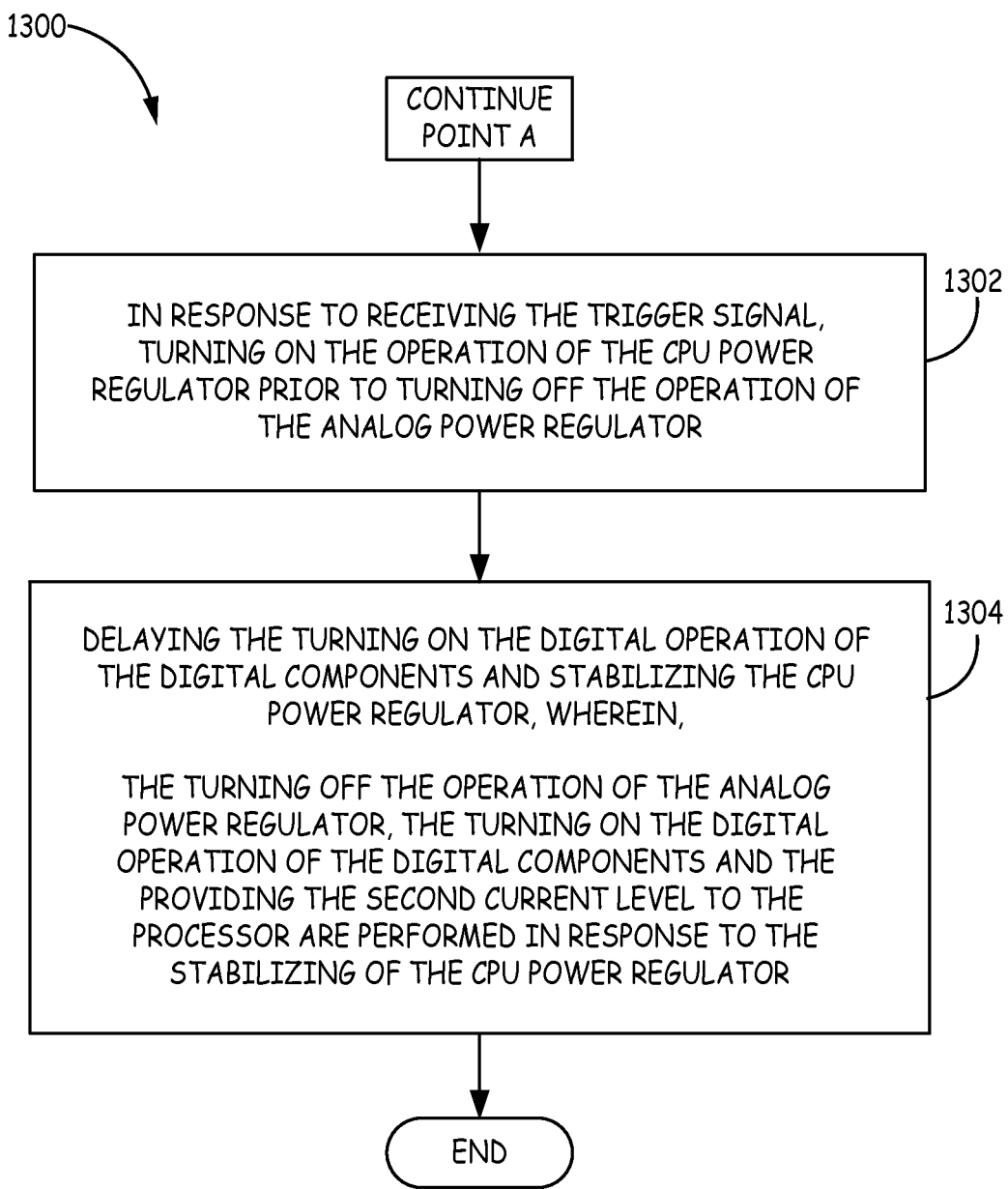
FIG. 13 illustrates another example methodology for regulating power consumption of an implantable device in accordance with aspects described herein.

FIG. 13 presents a method 1300 that is a continuation of method 1200 at continue point A. Acts 1302 and 1304 are performed in response to receiving in response to the receiving the trigger signal (e.g., associated with act 1204 of process 1200). At 1302, the operation of the CPU power regulator is turned on prior to turning off the operation of the analog power regulator. At 1304, the turning on the digital operation of the digital components is delayed (e.g., using delay component 502), and the CPU power regulator is allowed to stabilize prior to the following: the turning off the operation of the analog power regulator, the turning on the digital operation of the digital components and the providing the second current level to the processor are performed in response to the stabilizing of the CPU power regulator.

Figure 14:
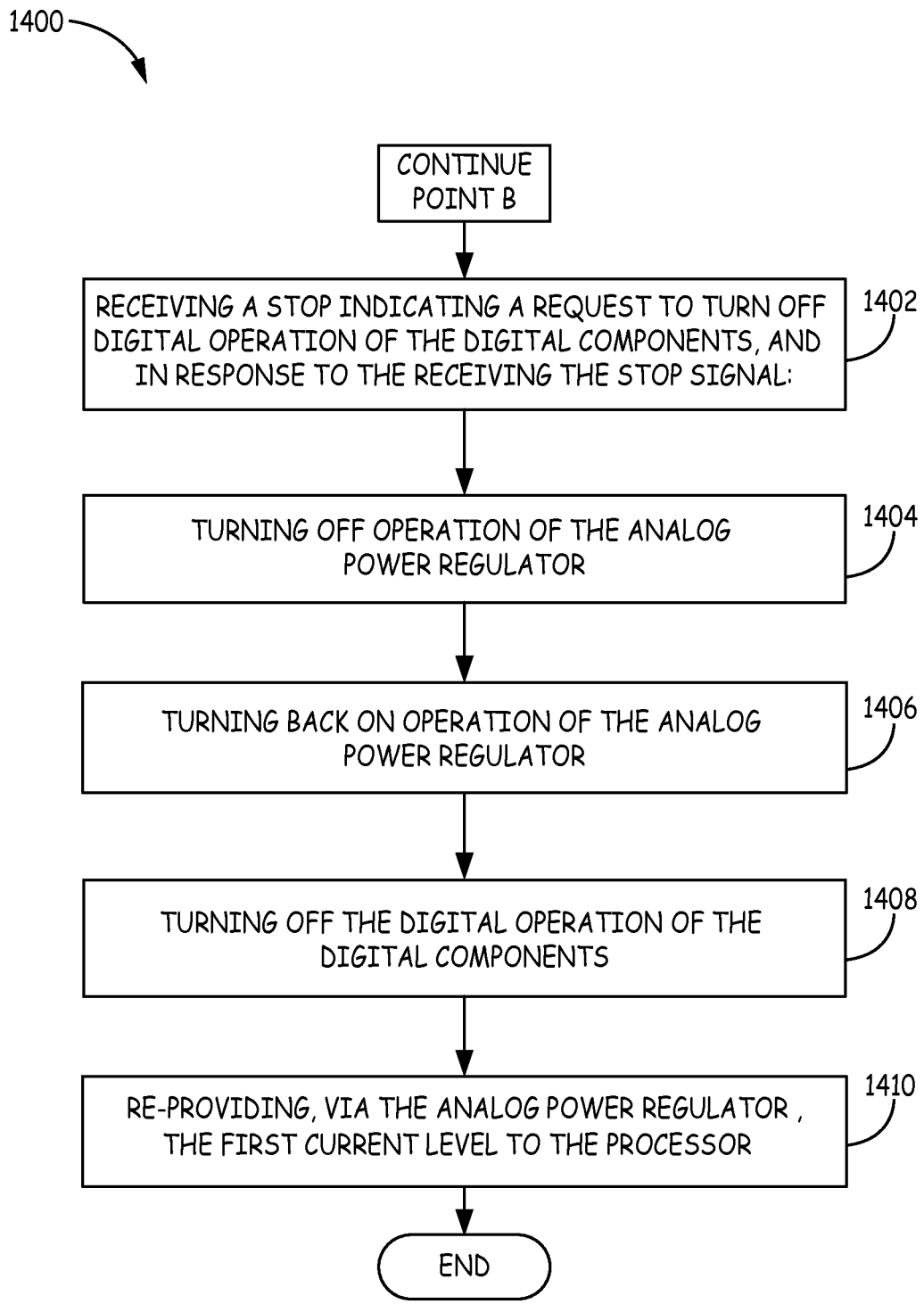
FIG. 14 illustrates another example methodology for regulating power consumption of an implantable device in accordance with aspects described herein.

FIG. 14 presents yet another method 1400 that is a continuance of method 1200 at continue point B. At 1402, a stop signal indicating a request to turn off digital operation of the digital components is received. Acts 1404-1410 are performed in response to the receiving the stop signal. At, 1404 operation of the CPU power regulator is turned off. At 1406, operation of the analog power regulator is turned back on. At 1408, the digital operation of the digital components is turned off, and at 1410, the first current level to is once again provided to the processor via the analog power regulator.

Exemplary Computing Device

As mentioned, advantageously, the techniques described in this disclosure can be associated with any suitable electronic device including but not limited to: an implantable device, a implantable medical device, a portable device and other computing devices. As described, in some aspects, the device can be a substantially small implantable medical device configured to wirelessly communicate with another device.

Figure 15:
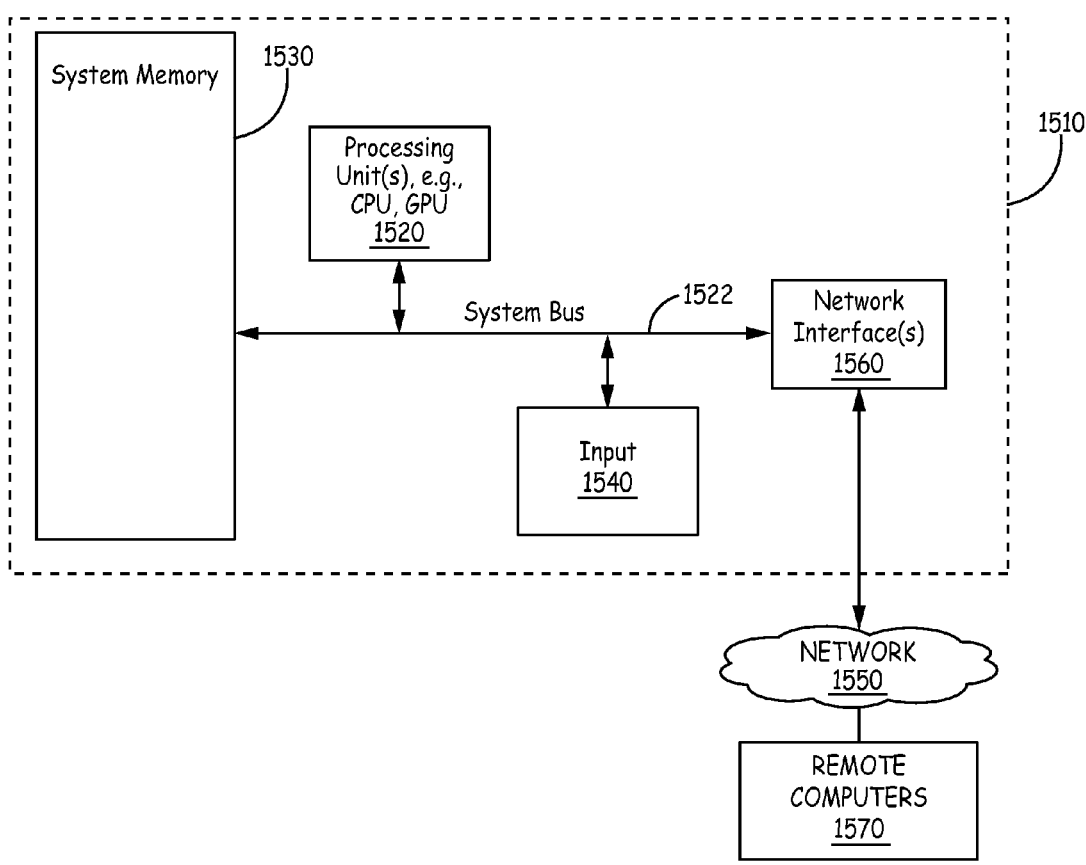
FIG. 15 is an illustration of a schematic diagram of an exemplary computing device with which one or more aspects described herein can be associated.

FIG. 15 illustrates an example of a suitable computing system environment 1500 in which one or aspects of the aspects described in this disclosure can be implemented. Components of computer 1510 can include, but are not limited to, a processing unit 1520, a system memory 1530, and a system bus 1522 that couples various system components including the system memory to the processing unit 1520.

Computer 1510 typically includes a variety of computer readable media and can be any available media that can be accessed by computer 1510. The system memory 1530 can include computer storage media in the form of volatile and/or nonvolatile memory such as read only memory (ROM) and/or random access memory (RAM). By way of example, and not limitation, memory 1530 can also include an operating system, application programs, other program components, and program data.

In an aspect, a user can enter commands and information into the computer 1510 through and input device 1540 (e.g., a remote wireless device, a keyboard, a keypad, a pointing device, a mouse, stylus, touchpad, touch screen, motion detector, camera, microphone or any other device that allows the user to interact with the computer 1510). The computer 1510 can operate in a networked or distributed environment using logical connections to one or more other remote computers, such as remote computer 1570. The remote computer 1570 can be a personal computer, a server, a router, a network PC, a peer device or other common network node, or any other remote media consumption or transmission device, and can include any or all of the elements described above relative to the computer 1510. For example, a remote computer can include reader devices, monitors, or programming devices. The logical connections depicted in FIG. 15 include a network 1550, such local area network (LAN) (e.g., a BLUETOOTH® network or near field communication (NFC) network) or a wide area network (WAN), but can also include other networks/buses e.g., cellular networks. Computer 1510 can include network interfaces 1560 to facilitate interfacing with a remote computer 1570 via a network 1550.

Computing devices typically include a variety of media, which can include computer-readable storage media and/or communications media, in which these two terms are used herein differently from one another as follows. Computer-readable storage media can be any available storage media that can be accessed by the computer, can be typically of a non-transitory nature, and can include both volatile and non-volatile media, removable and non-removable media. By way of example, and not limitation, computer-readable storage media can be implemented in connection with any method or technology for storage of information such as computer-readable instructions, program components, structured data, or unstructured data. Computer-readable storage media can include, but are not limited to, RAM, ROM, electrically erasable programmable read only memory (EEPROM), flash memory or other memory technology, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium. In various aspects, the computer-readable storage media can be, or be included within, the memory, the implantable device (or components thereof) as described herein.

On the other hand, communications media typically embody computer-readable instructions, data structures, program components or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals.

It is to be understood that the aspects described in this disclosure can be implemented in hardware, software, firmware, middleware, microcode, or any combination thereof. For a hardware aspect, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors and/or other electronic units designed to perform the functions described in this disclosure, or a combination thereof.

For a software aspect, the techniques described in this disclosure can be implemented with components or components (e.g., procedures, functions, and so on) that perform the functions described in this disclosure. The software codes can be stored in memory units and executed by processors.

What has been described above includes examples of one or more aspects. It is, of course, not possible to describe every conceivable combination of components or methodologies for purposes of describing the aforementioned aspects, but one of ordinary skill in the art can recognize that many further combinations and permutations of various aspects are possible. Accordingly, the described aspects are intended to embrace all such alterations, modifications and variations that fall within the spirit and scope of the appended claims.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

The aforementioned systems have been described with respect to interaction between several components. It can be appreciated that such systems and components can include those components or specified sub-components. Sub-components can also be implemented as components communicatively coupled to other components rather than included within parent components (hierarchical). Additionally, it is to be noted that one or more components can be combined into a single component providing aggregate functionality. Any components described in this disclosure can also interact with one or more other components not specifically described in this disclosure but generally known by those of skill in the art.

In addition to the various aspects described in this disclosure, it is to be understood that other similar aspects can be used or modifications and additions can be made to the described aspect(s) for performing the same or equivalent function of the corresponding aspect(s) without deviating there from. Still further, multiple processing chips or multiple devices can share the performance of one or more functions described in this disclosure, and similarly, storage can be provided across a plurality of devices. The invention is not to be limited to any single aspect, but rather can be construed in breadth, spirit and scope in accordance with the appended claims.

What is claimed is:

1. An implantable device, comprising:
 a substrate that forms at least part of a body of the implantable device; and
 a circuit disposed on or within the substrate and comprising:
  a high load power regulator configured to provide a first current level to one or more components of the implantable device;
  a low load power regulator configured to provide a second current level to the one or more components of the implantable device, wherein the second current level is lower that the first current level; and
  a regulator switch configured to simultaneously enable or disable current draw from the high load power regulator and the low load power regulator as a function of power state and associated power requirement of the one or more components of the implantable device, such that the first current level can be provided to at least a first of the one or more components while simultaneously providing the second current level to at least a second of the one or more components.

2. The implantable device of claim 1, wherein the one or more components include a high power component and a low power component, wherein the high power component employs a higher current for operation than the low power component.

3. The implantable device of claim 2, wherein the regulator switch is configured to enable current draw from the low load power regulator and disable current draw from the high load power regulator in response to the high power component being in a passive state.

4. The implantable device of claim 2, wherein the regulator switch is configured to disable current draw from the low load power regulator and enable current draw from the high load power regulator in response to the high power component being in an active state.

5. The implantable device of claim 2, wherein the high power component is a digital component and the low power component is an analog component.

6. The implantable device of claim 1, further comprising one or more power sources configured to provide power to the high load power regulator and the low load power regulator.

7. The implantable device of claim 6, wherein the one or more power sources includes a first battery coupled to the high load power regulator and a second battery coupled to the low load power regulator.

8. A power regulation system for an implantable medical device, comprising:
 a processor operatively coupled to the implantable medical device;
 a non-transitory computer readable medium that stores computer executable components, wherein the non-transitory computer readable medium comprises flash memory;
 a central processing unit (CPU) power regulator configured to provide a first current level to the processor;
 an analog power regulator configured to provide a second current level to the processor, wherein the second current level is lower that the first current level;
 a flash power regulator configured to provide a third current level to the flash memory; and
 a regulator switch configured to enable or disable current draw from the CPU power regulator and the analog power regulator as a function of a power state of the processor, wherein the third current level is higher than the first current level, and wherein the regulator switch is configured to enable current draw from the flash power regulator and disable current draw from the analog power regulator and CPU power regulator in response to programming or erasing of the flash memory.

9. The power regulation system of claim 8, wherein the CPU power regulator is configured to provide the first current level for digital components of the processor and the analog power regulator is configured to provide the second current level for analog components of the processor.

10. The power regulation system of claim 8, wherein the analog power regulator is further configured to provide the second current level to analog components of the implantable medical device.

11. The system of claim 8, wherein the processor has a duty cycle from about 0.1 percent to about 5.0 percent and the regulator switch is configured to enable or disable current draw from the CPU power regulator and the analog power regulator as a function of the duty cycle.

12. The system of claim 8, wherein the regulator switch is configured to enable current draw from the analog power regulator and disable current draw from the CPU power regulator in response to the processor being in an off state.

13. The system of claim 8, wherein the regulator switch is configured to disable current draw from the analog power regulator and enable current draw from the CPU power regulator in response to the processor being in an on state.

14. The system of claim 8, wherein the CPU power regulator is configured to turn on before the processor is turned on in response to receipt of a signal indicating an event that requires the processor to be turned on, the system further comprising:
 a delay component configured to effect a delay to digital operation of the processor to allow the CPU power regulator to stabilize, wherein the regulator switch is configured to enable current draw from the CPU power regulator after the CPU power regulator stabilizes.

15. The system of claim 14, further comprising a high frequency oscillator configured to provide a first dynamic current to the CPU regulator in response to turning on of the CPU power regulator.

16. The system of claim 8, wherein the CPU regulator is configured to provide greater than about 40.0 microamperes (μA) of current to the processor.

17. The system of claim 8, wherein the analog power regulator is configured to provide less than about 15.0 microamperes (μA) of current to the processor.

18. The system of claim 8, further comprising:
at least one battery, wherein the CPU power regulator and the analog power regulator are configured to regulate power drawn from the at least one battery.

19. The system of claim 8, wherein the CPU power regulator is configured to regulate power supplied from a first battery and the analog power regulator is configured to regulate power supplied from a charge pump coupled to a second battery.

20. The system of claim 8, wherein the processor, the non-transitory computer readable medium, the CPU power regulator, the analog power regulator and the at least one battery are encapsulated in a housing of the implantable medical device.

21. The system of claim 8, wherein the regulator switch comprises a multiplexor.

22. A method comprising:
providing, via an analog power regulator, a first current level to at least one analog component of the processer of an implantable device in response to digital components of the processor being in an off state;
receiving a trigger signal indicating a request to turn on digital operation of the digital components, and in response to the receiving the trigger signal:
turning on operation of a central processing unit (CPU) power regulator;
turning on the digital operation of the digital components;
providing, via the CPU power regulator, a second current level to the processor, wherein the second current level is higher than the first current level;
simultaneously enabling current draw from the analog power regulator and the CPU power regulator such that the first current level can be provided to the at least one analog component and the second current level can be provided to digital components as a function of power state and associated power requirement of the components of the processor; and
powering the digital operation of the digital components via the CPU power regulator.

23. The method of claim 22, further comprising, in response to the receiving the trigger signal:
turning on the operation of the CPU power regulator prior to turning off the operation of the analog power regulator; and
delaying the turning on the digital operation of the digital components and stabilizing the CPU power regulator, wherein the turning off the operation of the analog power regulator, the turning on the digital operation of the digital components and the providing the second current level to the processor are performed in response to the stabilizing the CPU power regulator.

24. The method of claim 23, wherein the turning on the operation of the CPU power regulator comprises providing the CPU power regulator a first dynamic current via a high frequency oscillator.

25. The method of claim 22, further comprising:
receiving a stop indicating a request to turn off digital operation of the digital components, and in response to the receiving the stop signal:
turning off operation of the CPU power regulator;
turning back on operation of the analog power regulator;
turning off the digital operation of the digital components; and
re-providing, via the analog power regulator, the first current level to the processor.

26. The method of claim 22, wherein the providing the first current level to the processor further comprises powering operation of analog components of the processor.

27. The method of claim 22, wherein the digital operation is powered via a regulator switch, by enabling current draw from the CPU power regulator, wherein the regulator switch comprises a multiplexor.

28. A power regulation system for an implantable medical device, comprising:
a processor operatively coupled to the implantable medical device;
a non-transitory computer readable medium that stores computer executable components;
a central processing unit (CPU) power regulator configured to provide a first current level to the processor, wherein the CPU power regulator is configured to turn on before the processor is turned on in response to receipt of a signal indicating an event that requires the processor to be turned on;
an analog power regulator configured to provide a second current level to the processor, wherein the second current level is lower that the first current level;
a regulator switch configured to enable or disable current draw from the CPU power regulator and the analog power regulator as a function of a power state of the processor;
a delay component configured to effect a delay to digital operation of the processor to allow the CPU power regulator to stabilize, wherein the regulator switch is configured to enable current draw from the CPU power regulator after the CPU power regulator stabilizes; and
a high frequency oscillator configured to provide a first dynamic current to the CPU regulator in response to turning on of the CPU power regulator, wherein the high frequency oscillator and the CPU power regulator are configured to turn off and the regulator switch are configured to enable current draw from the analog power regulator in response to receipt of a signal indicating completion of the event.

\* \* \* \* \*